United States Patent
Kuzma et al.

(10) Patent No.: US 7,759,312 B2
(45) Date of Patent: *Jul. 20, 2010

(54) DELIVERY OF DRY FORMULATIONS OF OCTREOTIDE

(75) Inventors: Petr Kuzma, Princeton, NJ (US); Stefanie Decker, Princeton, NJ (US)

(73) Assignee: Endo Pharmaceuticals Solutions Inc., Chadds Ford, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/171,999

(22) Filed: Jul. 11, 2008

(65) Prior Publication Data

US 2009/0035343 A1 Feb. 5, 2009

Related U.S. Application Data

(63) Continuation-in-part of application No. 11/372,749, filed on Mar. 10, 2006, now Pat. No. 7,452,868.

(60) Provisional application No. 60/660,930, filed on Mar. 11, 2005.

(51) Int. Cl.
*A61K 38/08* (2006.01)
*A61K 9/52* (2006.01)

(52) U.S. Cl. .................... 514/16; 424/422; 424/461; 424/462

(58) Field of Classification Search ............... None
See application file for complete search history.

(56) References Cited

U.S. PATENT DOCUMENTS

| | | | |
|---|---|---|---|
| 4,131,604 A | 12/1978 | Szycher | |
| 4,285,987 A | 8/1981 | Ayer et al. | |
| 4,386,039 A | 5/1983 | Szycher | |
| 4,523,005 A | 6/1985 | Szycher | |
| 4,743,673 A | 5/1988 | Johnston et al. | |
| 4,751,133 A | 6/1988 | Szycher et al. | |
| 4,954,587 A | 9/1990 | Mueller | |
| 4,959,217 A | 9/1990 | Sanders et al. | |
| 5,254,662 A | 10/1993 | Szycher et al. | |
| 5,266,325 A | 11/1993 | Kuzma et al. | |
| 5,273,752 A | 12/1993 | Ayer et al. | |
| 5,292,515 A | 3/1994 | Moro et al. | |
| 5,342,622 A | 8/1994 | Williams et al. | |
| 5,354,835 A | 10/1994 | Blair | |
| 5,431,921 A | 7/1995 | Thombre | |
| 5,464,933 A | 11/1995 | Bolognesi et al. | |
| 5,468,811 A | 11/1995 | Moro et al. | |
| 5,614,223 A | 3/1997 | Sipos | |
| 5,637,309 A | 6/1997 | Tajima et al. | |
| 5,686,411 A | 11/1997 | Gaeta et al. | |
| 5,756,127 A | 5/1998 | Grisoni et al. | |
| 5,817,343 A | 10/1998 | Burke | |
| 5,854,127 A | 12/1998 | Pan | |
| 5,876,761 A | 3/1999 | Bodmer et al. | |
| 5,894,458 A | 4/1999 | Takizawa et al. | |
| 6,087,334 A | 7/2000 | Beeley et al. | |
| 6,143,718 A | 11/2000 | Kolterman et al. | |
| 6,159,490 A | 12/2000 | Deghenghi | |
| 6,313,254 B1 | 11/2001 | Meijs et al. | |
| 6,337,318 B1 | 1/2002 | Trigg et al. | |
| 6,361,797 B1 | 3/2002 | Kuzma et al. | |
| 6,417,164 B1 | 7/2002 | Kolterman et al. | |
| 6,579,851 B2 | 6/2003 | Goeke et al. | |
| 6,602,694 B1 | 8/2003 | Albrandt et al. | |
| 6,770,623 B1 | 8/2004 | Chang et al. | |
| 6,872,700 B1 | 3/2005 | Young et al. | |
| 6,942,264 B1 | 9/2005 | Mendez | |
| 6,969,480 B2 | 11/2005 | Dalton et al. | |
| 7,008,927 B2 | 3/2006 | Ochiai et al. | |
| 7,056,887 B2 | 6/2006 | Coolidge et al. | |
| 7,101,853 B2 | 9/2006 | Young et al. | |
| 7,105,489 B2 | 9/2006 | Hathaway | |
| 7,115,569 B2 | 10/2006 | Beeley et al. | |
| 7,118,737 B2 | 10/2006 | Kochendoerfer et al. | |
| 7,153,825 B2 | 12/2006 | Young et al. | |
| 7,220,721 B1 | 5/2007 | Beeley et al. | |
| 7,259,136 B2 | 8/2007 | Hathaway et al. | |
| 7,271,238 B2 | 9/2007 | Gaeta et al. | |
| 7,452,868 B2 | 11/2008 | Kuzma et al. | |
| 2002/0141985 A1 | 10/2002 | Pittner et al. | |
| 2003/0036504 A1 | 2/2003 | Kolterman et al. | |
| 2004/0002454 A1 | 1/2004 | Coolidge et al. | |
| 2005/0037078 A1 | 2/2005 | Kuo et al. | |
| 2005/0287320 A1 | 12/2005 | Dalton et al. | |
| 2006/0019903 A1 | 1/2006 | Kuzma et al. | |
| 2006/0030528 A1 | 2/2006 | Hathaway et al. | |
| 2006/0035836 A1 | 2/2006 | Coolidge et al. | |
| 2006/0067911 A1 | 3/2006 | Nilsson et al. | |

(Continued)

FOREIGN PATENT DOCUMENTS

EP 0 246 653 A2 11/1987

(Continued)

OTHER PUBLICATIONS

O'Donnell et al. "Therapeutic potential of a long acting somatostatin analogue in gastrointestinal diseases," Gut, 1989, 30, 1165-1172.*
Prommer, "Established and potential therapeutic applications of octreotide in palliative care," Support Care Cancer (2008) 16:1117-1123.*
Eurasian Patent Office Decision on Patentability corresponding to EU 200701956/28, dated Jan. 21, 2009, 6 pages.
New Zealand Patent Office Examination Report corresponding to NZ 561400, dated Jul. 28, 2009, 2 pages.

(Continued)

*Primary Examiner*—Christina Bradley
(74) *Attorney, Agent, or Firm*—Gilberto M. Villacorta; Jeffrey R. Lomprey; Foley & Lardner LLP

(57) ABSTRACT

Methods and devices are described for delivering octreotide to a patient, comprising implanting a controlled release composition for delivering octreotide, wherein the composition does not require hydration prior to implantation, and wherein the composition optionally comprises a release agent.

17 Claims, 21 Drawing Sheets

U.S. PATENT DOCUMENTS

| | | |
|---|---|---|
| 2006/0122106 A1 | 6/2006 | Gedulin et al. |
| 2006/0148713 A1 | 7/2006 | Beeley et al. |
| 2006/0204540 A1 | 9/2006 | Kuzma et al. |
| 2006/0233747 A1 | 10/2006 | Kochendoerfer et al. |
| 2006/0293232 A1 | 12/2006 | Levy et al. |
| 2007/0010656 A1 | 1/2007 | Beeley et al. |
| 2008/0311170 A1 | 12/2008 | Kuzuma et al. |
| 2009/0087470 A1 | 4/2009 | Kuzma et al. |

FOREIGN PATENT DOCUMENTS

| | | |
|---|---|---|
| EP | 0 314 206 | 5/1989 |
| EP | 0 551 699 A1 | 7/1993 |
| EP | 0 645 136 A2 | 3/1995 |
| JP | 05-269759 | 10/1993 |
| JP | 05-269760 A | 10/1993 |
| JP | 07-097338 A | 4/1995 |
| JP | 07-252166 A | 10/1995 |
| JP | 11-506730 T | 6/1999 |
| JP | 2002-535452 T | 10/2002 |
| NZ | 245383 | 5/1994 |
| WO | WO-96/40049 A1 | 12/1996 |
| WO | WO-98/44964 | 10/1998 |
| WO | WO-00/44356 A1 | 8/2000 |
| WO | WO-02/078597 A2 | 10/2002 |
| WO | WO-2005/013936 A2 | 2/2005 |
| WO | WO-2006/099288 A3 | 9/2006 |
| WO | WO-2007/028394 | 3/2007 |
| WO | WO-2008/134475 A2 | 11/2008 |

OTHER PUBLICATIONS

Chinese Office Action corresponding to CN 2006800160292, dated Sep. 4, 2009, 8 pages.
U.S. Appl. No. 12/490,971, filed Jun. 24, 2009, Kuzma et al.
U.S. Appl. No. 12/490,979, filed Jun. 24, 2009, Kuzma et al.
"RxMed: Pharmaceutical Information—Sandostatin LAR DEPOT" [online], Jan. 6, 2003 [retrieved Aug. 16, 2006]; http://www.rxmed.com.
A.R. Gennaro, Remington: The Science and Practice of Pharmacy, 19th Edition, p. 1662.
Bevan et al., Primary Medical Therapy for Acromegaly: An Open, Prospective, Multicenter Study of the Effects of Subcutaneous and Intramuscular Slow-Release Octreotide on Growth Hormone, Insulin-Like Growth Factor-L, and Tumor Size, J. Clin. Endoc. Metab,. 87(10), 2002, pp. 4554-4563.
Chertin et al., "An Implant Releasing the Gonadotropin Hormone-Releasing Hormone Agonist Histrelin Maintains Medical Castration for Up to 30 Months in Metastic Prostate Cancer," Journal of Urology, Baltimore,MD,US,vol. 163.
International Search Report and Written Opinion, PCT/US2009/050215, dated Nov. 25, 2009, 11 pgs.
International Search Report, PCT/US00/01664, dated Jul. 13, 2000, 1 pg.
International Search Report, PCT/US2006/08891, dated Dec. 4, 2006, 2 pgs.
International Search Report, PCT/US2005/021368, dated Oct. 23, 2006, 3 pgs.
International Search Report, PCT/US2008/061511, dated Nov. 8, 2009, 2 pgs.
Lan NaLee, "Volume of Blood in a Human," from http://hypertextbook.com/facts/1998/LanNaLee.shtml, (1998) updated (2001).
Langer, "Implantable Controlled Release Systems," Pharmac. Ther. (1983), vol. 21, p. 35-51.
P. Kuzma et al., U.S. PTO Office Action, U.S. Appl. No. 11/155,822 dated Jan. 22, 2008, 12 pgs.
P. Kuzma et al., U.S. PTO Office Action, U.S. Appl. No. 11/155,822 dated Feb. 18, 2009, 11 pgs.
P. Kuzma et al., U.S. PTO Office Action, U.S. Appl. No. 11/155,822 dated Oct. 13, 2009, 21 pgs.
Schlegel et al., "Effective Long-Term Androgen Suppression in Men with Prostate Cancer Using a Hydrogel Implant with the GnRH Agonist Histrelin," Urology,vol. 58.
Barradell, L. B. et al., "Histrelin: A Review of its Pharmacological Properties and Therapeutic Role in Central Precocious Puberty," Drugs, vol. 45, No. 4, Apr. 1993, pp. 570-588; published by Adis International Limited.
English Translation of Examiner's Final Decision of Rejection for Japanese Appln. No. 2008-501025 dated Dec. 1, 2009.
Examination Report received for Australian Appln. No. 561400 dated Dec. 16, 2009.
Feuillan, P. P. et al., "Follow-up of children and young adults after GnRH-agonist therapy for central precocious puberty," J. Endocrinol. Invest., vol. 24, 2001, pp. 734-736; published by Editrice Kurtis.
First Notice of Reasons for Rejection and translation received for Japanese Appln. No. 2000-595660 dated Jun. 9, 2009.
International Search Report and Written Opinion for PCT/US/2009/050215 dated Nov. 25, 2009.
International Search Report and Written Opinion for PCT/US2009/048484 dated Nov. 26, 2009.
Kim, S. W., et al., "Water in Polymers—Solute Permeation Through Hydrogel Membranes," ACS Symposium Series, 127 (1980), pp. 347-359.
Nielsen, P. E., et al., "Peptide Nucleic Acid (PNA). A DNA Mimic with a Peptide Backbone," Bioconjugate Chem., vol. 5, No. 1, 1994, pp. 3-7.
Non-final Office Action received for U.S. Appl. No. 11/372,749 dated Feb. 5, 2008.
Notice of Allowance received for U.S. Appl. No. 11/372,749 dated Aug. 11, 2008.
Office Action received in Israel Appln. No. 185800 dated Jan. 21, 2010.
Palii, et al., "Medical treatment of diabetic retinopathy with somatostatin analogues," Expert Opinion Investig. Drugs, vol. 16, No. 1, (2007), pp. 73-82.
Pawlikowski, et al., "Perspectives of new potential therapeutic applications of somatostatin analogs," Neuroendocrinology Letters, vol. 24, Nos. 1/2, Feb.-Apr. 2003, pp. 21-27.
Pierard-Franchimont, et al., "Incidental Control of Rosacea by Somatostatin," Dermatology, (2003) 206:249-251.
Refojo, M. F., et al., "Microscopic Desternination of the Penetration of Proteins and Polysaccharides into Poly(hydroxyethyl Methacrylate) and similar Hydrogels," Journal of Polymer Science, Polymer Symposium, vol. 66, (1979), pp. 227-237.
Higuchi, et al., *Pro-Drugs as Novel Drug Delivery Systems: A.C.S Symposium Series*, American Chemical Society, Washington, DC, 1975.
Roche, ed., *Bioreversible Carriers in Drug Design: Theory and Application*, Pergamon Press, New York, 1987.
Berge, et al., "Pharmaceutical Salts," *Journal of Pharmaceutical Sciences*, vol. 66, No. 1, Jan. 1977, pp. 1-19.

* cited by examiner

DELIVERY OF DRY FORMULATIONS OF OCTREOTIDE

RELATED APPLICATIONS

This application is a Continuation-In-Part (CIP) of U.S. application Ser. No. 11/372,749, filed Mar. 10, 2006, which claims the benefit of U.S. Provisional Application Ser. No. 60/660,930, filed Mar. 11, 2005. The entire contents of these applications are incorporated herein by reference.

BACKGROUND OF THE INVENTION

Acromegaly is a hormonal disorder that results when the pituitary gland produces excess growth hormone (GH). It most commonly affects middle-aged adults and can result in serious illness and premature death. Once diagnosed, acromegaly is treatable in most patients, but because of its slow and often insidious onset, it frequently is not diagnosed correctly. The most serious health consequences of acromegaly are diabetes mellitus, hypertension and increased risk of cardiovascular disease. Patients with acromegaly are also at increased risk for polyps of the colon that can develop into cancer. When GH-producing tumors occur in childhood, the disease that results is called gigantism rather than acromegaly. Fusion of the growth plates of the long bones occurs after puberty so that development of excessive GH production in adults does not result in increased height. Prolonged exposure to excess GH before fusion of the growth plates causes increased growth of the long bones and increased height.

Acromegaly is caused by prolonged overproduction of growth hormone (GH) by the pituitary gland. The pituitary is a small gland at the base of the brain that produces several important hormones to control body functions such as growth and development, reproduction, and metabolism. GH is part of a cascade of hormones that, as the name implies, regulates the physical growth of the body. This cascade begins in a part of the brain called the hypothalamus, which makes hormones that regulate the pituitary. One of these, growth hormone-releasing hormone (GHRH), stimulates the pituitary gland to produce GH. Another hypothalamic hormone, somatostatin, inhibits GH production and release. Secretion of GH by the pituitary into the bloodstream causes the production of another hormone, called insulin-like growth factor 1 (IGF-1), in the liver. IGF-1 is the factor that causes the growth of bones and other tissues of the body. IGF-1, in turn, signals the pituitary to reduce GH production. GHRH, somatostatin, GH and IGF-1 levels in the body are tightly regulated by each other, and their levels are influenced by environmental stimuli such as sleep, exercise, stress, food intake and blood sugar levels. If the pituitary produces GH independent from the normal regulatory mechanisms, the level of IGF-1 would rise, leading to bone growth and organ enlargement. Excess GH also causes changes in sugar and lipid metabolism and can cause diabetes.

In over 90% of acromegaly patients, the overproduction of GH is caused by a benign tumor of the pituitary gland, called an adenoma. These tumors produce excess GH and, as they expand, compress surrounding brain tissues, such as the optic nerves. This expansion causes the headaches and visual disturbances that are often symptoms of acromegaly. In addition, compression of the surrounding normal pituitary tissue can alter production of other hormones, leading to changes in menstruation and breast discharge in women and impotence in men.

In some patients, acromegaly is caused not by pituitary tumors but by tumors of the pancreas, lungs and adrenal glands. These tumors lead to an excess of GH, either because they produce GH themselves or, more frequently, because they produce GHRH, the hormone that stimulates the pituitary to make GH. In these patients, the excess GHRH can be measured in the blood and establishes that the cause of the acromegaly is not due to a pituitary defect. When these non-pituitary tumors are surgically removed, GH levels fall and the symptoms of acromegaly improve.

Acromegaly treatment regimens include reducing GH production to normal levels to relieve the pressure that the growing pituitary tumor exerts on the surrounding brain areas, to preserve normal pituitary function, and to reverse or ameliorate the symptoms of acromegaly. Treatment options include surgical removal of the tumor, drug therapy and radiation therapy of the pituitary.

Octreotide has been demonstrated to be effective in the management of acromegaly. GH levels usually decrease within two hours following a subcutaneous octreotide injection. Octreotide results in a decrease in GH and IGF-1 levels in a majority of patients with normalization of IGF-1 levels in up to 60% of patients, indicating biochemical remission. Most patients note a marked improvement in their symptoms of acromegaly including headaches, joint pains and diaphoresis very soon after starting octreotide therapy. Octreotide is currently available as Sandostatin LAR® Depot, which is, upon reconstitution, a suspension of micro spheres containing octreotide acetate. Sandostatin LAR® Depot is the only medication indicated for the long-term maintenance therapy in acromegalic patients. It is also indicated for the long-term treatment of severe diarrhea and flushing episodes associated with metastatic carcinoid tumors and profuse water diarrhea associated with VIP-secreting tumors. Sandostatin LAR® Depot is administered via intramuscular injection every four weeks, following a titration period. Octreotide acetate has also been available in an immediate-release formulation, Sandostatin® Injection solution, which is required to be administered by injection three times daily.

In patients who do not have a significant reduction in GH levels in response to intermittent octreotide injections, more frequent dosing of octreotide may result in a greater clinical response. Octreotide may be administered continuously by a subcutaneous pump to patients with refractory acromegaly to prevent escape of GH between injections.

In light of the efficacy of octreotide for treating acromegaly and lack of a controlled-release treatment method and formulation of octreotide, there is a clear need for a formulation and delivery method that can deliver octreotide over a period of time at a controlled rate to avoid the complications of a patient's having to suffer, for example, multiple periodic injections.

SUMMARY OF THE INVENTION

The present invention relates generally to an octreotide pharmaceutical composition that can be used to treat individuals affected with hormonal disorders. The present invention is preferably formulated as a controlled-release formulation. In particular, the present invention is based on the unexpected discovery that octreotide can be released at a controlled rate using an implantable device, e.g., an implantable device that does not require priming prior to implantation.

In one embodiment, the present invention is directed to a method of delivering octreotide to a subject with a substantially zero-order release profile over an extended period of time, but no less than about six months, the method comprising subcutaneously implanting in the subject at least one implantable device, wherein the at least one implantable device comprises a composition comprising octreotide, wherein the composition is encased in a hydrophilic polymer, and wherein the implantable device is implanted in a dry state, such that the subject receives on a daily basis over a period of at least about six months dose amounts of octreotide, which are effective to treat the subject. In a particular embodiment, the hydrophilic polymer comprises one or more polyurethane-based polymers or methacrylate-based polymers. In one embodiment, the octreotide is in free form, salt form or in the form of a complex thereof, e.g., octreotide acetate. In a particular embodiment, the subject is afflicted with a GH or IGF-1 hormone disorder or its symptoms, e.g., acromegaly. In a particular embodiment, the subject receives octreotide at an average rate ranging from about 75 µg per day to about 300 µg per day over a period of at least about six months. In a particular embodiment, the dose amounts of octreotide received by the subject result in octreotide serum levels ranging from about 0.5 ng/ml to about 2 ng/ml. In a particular embodiment, the subject receives an effective amount of octreotide for a period of at least about twelve months. In a particular embodiment, the dose amounts of octreotide received by the subject result in octreotide serum levels ranging from about 0.8 ng/ml to about 1.8 ng/ml. In a particular embodiment, the dose amounts of octreotide received by the subject result in $C_{max}$ for octreotide serum levels below about 1.3 ng/ml. In a particular embodiment, the dose amounts of octreotide received by the subject result in $C_{max}$ for octreotide serum levels below about 1.0 ng/ml. In a particular embodiment, release of octreotide occurs at least three to about ten days after implantation. In a particular embodiment, the subject is afflicted with a condition selected from the group consisting of: carcinoid syndrome, VIPomas, neuroendocrine tumors, proliferative diabetic retinopathy, rosacea, pancreatitis, gastrointestinal bleeding, pancreatic and intestinal fistulas, Graves-Basedow opthalmopathy, glaucoma, and symptoms associated with chemotherapy or AIDS.

The present invention provides a therapeutically-effective amount of octreotide over an extended period of time, preferably at least about two months, more preferably about six months and up to about two years. The present invention also provides compositions that provide controlled-release of octreotide over at least about two months, preferably about six months, and up to about two years.

Embodiments of the present invention relate to a pharmaceutical composition comprising octreotide or salts, prodrugs or derivatives thereof, which can be used in the effective treatment of various diseases and conditions.

DETAILED DESCRIPTION OF THE INVENTION

Figure 1:
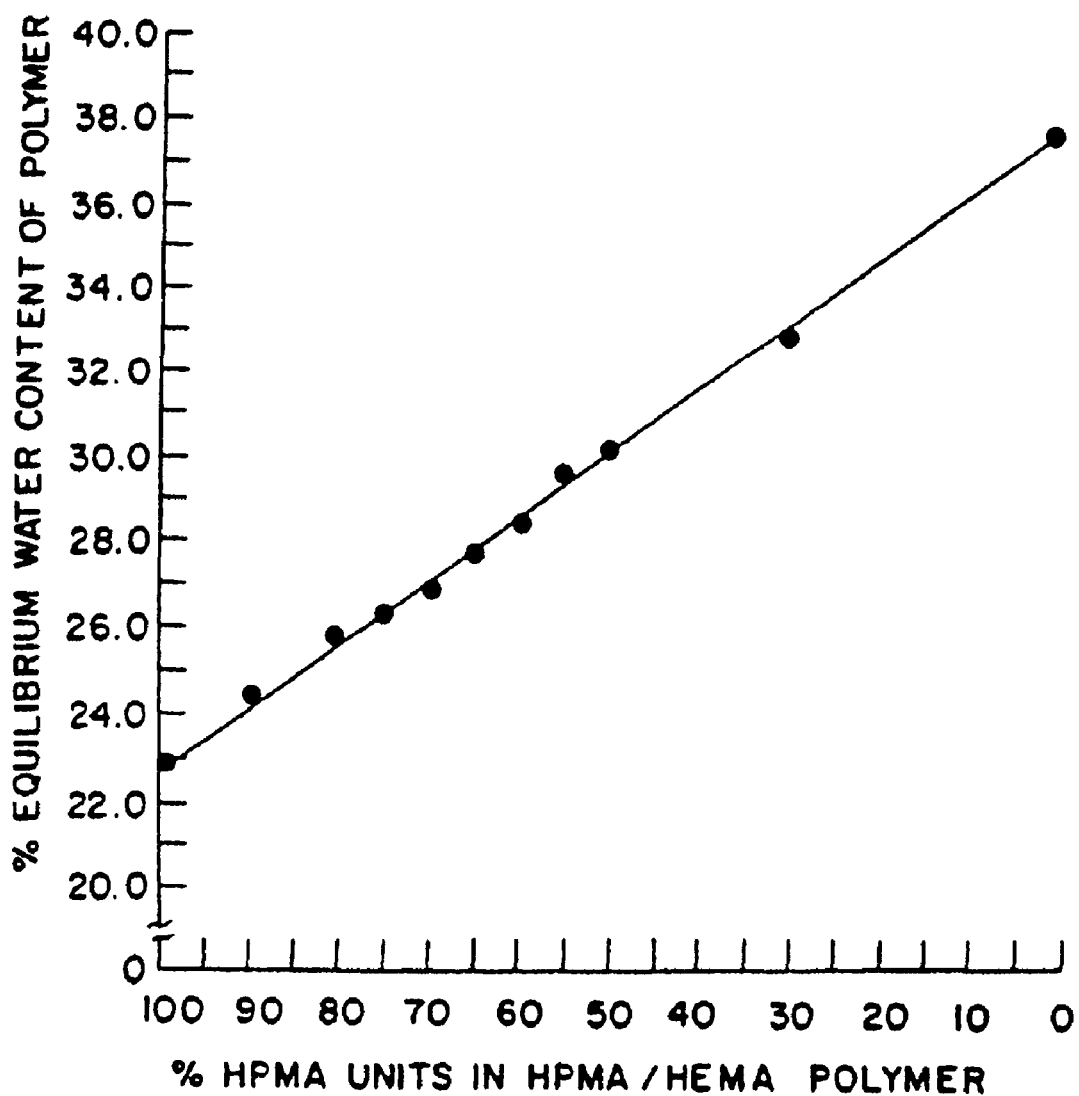
FIG. 1 is a graph showing the linear relationship between the equilibrium water content vs. the weight percent content of hydroxypropyl methacrylate (HPMA) units in crosslinked HEMA/HPMA polymers at their maximum state of hydration.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims. The terms used herein have meanings recognized and known to those of skill in the art, however, for convenience and completeness, particular terms and their meanings are set forth below.

The singular forms "a", "an", and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference to the extent they support the present invention. Nothing herein is to be construed as an admission that the invention is not entitled to antedate such disclosure by virtue of prior invention.

As used herein, the term "about: means plus or minus 10% of the numerical value of the number with which it is being used. For example, about 50% means in the range of 45%-55%.

"Controlled-release formulation" refers to a formulation designed to consistently release a predetermined, therapeutically-effective amount of drug or other active agent such as a polypeptide or a synthetic compound over an extended period of time, with the result being a reduction in the number of treatments necessary to achieve the desired therapeutic effect. A controlled-release formulation decreases the number of treatments necessary to achieve a desired effect in terms of decreased growth hormone levels or decreased IGF-1 levels, or an improvement in symptoms associated with, for example, acromegaly including but not limited to abnormal growth, carcinoid syndrome, VIPomas (Vasoactive Intestinal Peptide Secreting Adenomas), neuroendocrine tumors (specifically treating the symptoms of flushing and diarrhea), proliferative diabetic retinopathy, rosacea, pancreatitis, gastrointestinal bleeding, pancreatic and intestinal fistulas, Graves-Basedow opthalmopathy, glaucoma, or treating symptoms of chemotherapy and AIDS. The controlled-release formulations of the present invention achieve a desired pharmacokinetic profile in a subject, preferably commencement of the release of the active agent substantially immediately after placement in a delivery environment, followed by consistent, sustained, preferably zero-order or near zero-order release of the active agent.

As used herein, the term "controlled-release" includes the predetermined, consistent release of active agent from the dosage formulation at a rate such that a therapeutically beneficial blood level below toxic levels of the active agent is maintained over a period, for example, of at least about two months, about six months or more (e.g., up to about two years).

The terms "patient" and "subject" mean all animals including humans. Examples of patients or subjects include humans, cows, dogs, cats, goats, sheep, and pigs.

The term "pharmaceutically acceptable salts, esters, amides, and prodrugs" as used herein refers to those carboxylate salts, amino acid addition salts, esters, amides, and prodrugs of the compounds of the present invention that are, within the scope of sound medical judgment, suitable for use in contact with the tissues of patients without undue toxicity, irritation, allergic response and the like. Their use is commensurate with a reasonable benefit/risk ratio, and is effective for their intended use. Zwitterionic forms, where possible, are also useful compounds of the invention. The compounds of the present invention additionally can exist, for example, in unsolvated as well as solvated forms with pharmaceutically acceptable solvents such as, for example, water, ethanol and the like. In general, the solvated forms are considered equivalent to the unsolvated forms for the purposes of the present invention.

The term "prodrug" refers to compounds that are rapidly transformed in vivo to yield the parent compounds of the above formula, for example, by hydrolysis in blood. A thorough discussion is provided in T. Higuchi and V. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetraethylammonium, methylamine, dimethylamine, trimethylamine, triethylamine, ethylamine and the like (See, for example, S. M. Barge et al., "Pharmaceutical Salts," *J. Pharm. Sci.*, 1977, 66:1-19, which is incorporated herein by reference in its entirety).

"Treatment" refers to the administration of medicine or the performance of medical procedures with respect to a patient, either for prophylaxis (prevention) or to cure the infirmity or malady in the instance where the patient is afflicted.

A "therapeutically effective amount" is an amount sufficient to decrease, prevent or ameliorate the symptoms associated with a medical condition. In the context of hormonal therapy it can also mean an amount sufficient to normalize body functions or hormone levels in disease or disorders. For example, a therapeutically effective amount of a controlled-release formulation of octreotide is a predetermined amount calculated to achieve the desired effect, e.g., to effectively decrease growth hormone or IGF-1 levels in a patient.

The present invention can be utilized to treat a variety of hormonal disorders, including, for example, acromegaly and gigantism, or other diseases, disorders or symptoms that are effectively treated with, for example, octreotide, e.g., carcinoid syndrome, VIPomas (Vasoactive Intestinal Peptide Secreting Adenomas), neuroendocrine tumors (specifically treating the symptoms of flushing and diarrhea), proliferative diabetic retinopathy, rosacea, pancreatitis, gastrointestinal bleeding, pancreatic and intestinal fistulas, Graves-Basedow opthalmopathy, glaucoma, or treating symptoms of chemotherapy and AIDS.

Acromegaly is characterized by a number of clinical features including enlargement of the hands and feet, facial changes including frontal bossing, enlarged mandible and increased dental spacing, arthralgias, diaphoresis, sleep apnea, hypertension, diabetes mellitus and hypertrophic cardiomyopathy. Tumors that cause acromegaly frequently cause local anatomic compression, resulting in, for example, visual field deficits, headaches, hypopituitarism, and cranial nerve palsies. There is a 2 to 5 fold increase in the mortality rate in acromegalic patients largely due to cardiovascular and cerebrovascular disease. There is also an increased rate of malignancy associated with acromegaly, with colon cancer the best characterized.

Carcinoid tumors usually appear in the appendix, bronchial tubes, colon, or small intestine and secrete chemicals that cause the dilation of blood vessels-such as serotonin. Vasodilation may be responsible for the symptoms usually observed with Carcinoid tumors—such as, for example, diarrhea, flushing and asthma. Depending on the hormones and biochemicals secreted by carcinoid tumors a number of symptoms can be present. These are collectively known as "Carcinoid Syndrome". Biochemically, people with Carcinoid tumors tend to produce more serotonin, using the amino acid tryptophan as a base-serotonin is further broken down in the body to product 5-hydroxy indole acetic acid (5-HIAA) which is seen in the urine of the majority of such patients.

Diagnostic tests on blood and urine would show a patient with a Carcinoid tumor-exhibits elevated urinary 5-HIAA, low blood tryptophan, high blood chromogranin A, and serotonin. Blood tests are also used to levels of histamine, bradykinin, neurone-specific enolase, calcitonin, Substance-P, neurokinin-A, and pancreatic polypeptide.

An "OctreoScan" is a scanning test used to identify carcinoid tumors and neuroendocrine tumors. This scan utilizes a radioactive octreotide derivative called pentetreotide. Post-injection, this concentrates in tissues expressing the somatostatin receptor. Neuroendocrine tumors over-express the receptor and are imaged using this test.

As used herein, the term "octreotide" refers generally to all compounds comprising the structure as shown, including various salt forms. Octreotide comprises an octapeptide with the following amino acid sequence: L-cysteinamide, D-phenylalanyl-L-cysteiny-L-phenylalanyl-D-tryptophyl-L-lysyl-L-threonyl-N-[2-hydroxy-1-(hydroxymethyl)propyl]-,cyclic (2→7)-disulfide; [R—(R*,R*)]. The structure of octreotide is shown below.

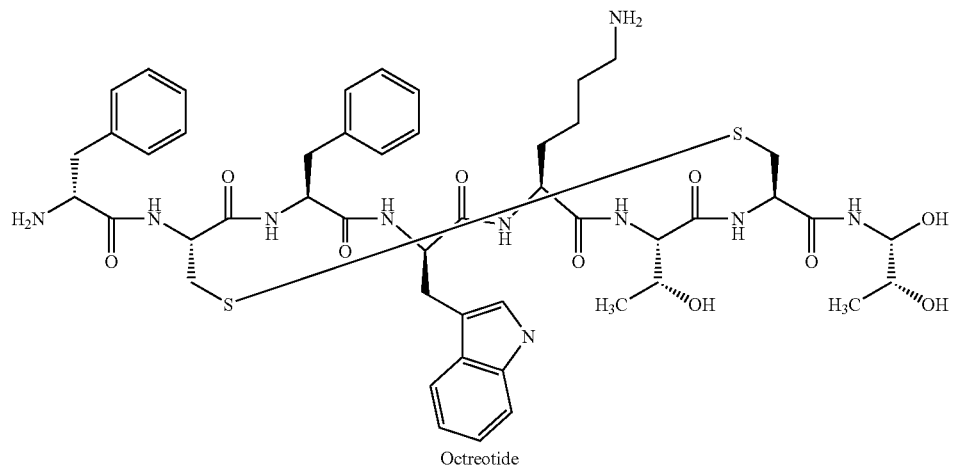

Octreotide

The chemical formula is $C_{49}H_{66}N_{10}O_{10}S_2$ and its molecular weight is 1019.3 Da. Its therapeutic category is gastric anti-secretory agent. The octreotide of the present invention can exist in, for example, a free form, a salt form or in the form of complexes thereof. Acid addition salts can be formed with, for example, organic acids, polymeric acids and inorganic acids. Acid addition salts include, for example, the hydrochloride and acetates. Complexes are formed, for example, from octreotide on addition of inorganic substances, e.g., inorganic salts or hydroxides such as Ca- and Zn-salts and/or addition of polymeric organic substances. The acetate salt is the preferred salt for formulations of the present invention.

Embodiments of the present invention provide a drug delivery device that can achieve the following objectives: a controlled-release rate (zero or about zero order release rate) to maximize therapeutic effects and minimize unwanted side effects; a convenient way to retrieve the device if it is necessary to end the treatment; and an increase in bioavailability with less variation in absorption and no first pass metabolism.

The controlled-release pharmaceutical composition comprising octreotide acetate can be part of a controlled-release hydrogel device. The composition of the present invention is capable of providing, upon administration to a patient, a release profile of octreotide extending over at least about two months, preferably at least about six months or more, e.g., up to about two years. Octreotide can be contained within the hydrogel, for example, and the formulation releases a therapeutically effective amount of octreotide over an extended period of time. The hydrogel can comprise a polymer selected from methacrylate-based polymers, polyurethane-based polymers and combinations thereof. A therapeutically effective amount is an amount of octreotide, preferably octreotide acetate, that when administered to a patient or subject, ameliorates a symptom of acromegaly. The formulation can further include pharmaceutically acceptable excipients.

When the compositions of the present invention are administered to a patient, the concentration of octreotide in the patient's plasma over time (release profile) can extend over a period of at least about two months, preferably about six months, and up to about two years. The compositions can provide a mean plasma concentration at steady state of octreotide in a human patient of from about 0.1 to about 9 ng/ml, about 5 ng/ml to about 1 ng/ml, about 1 to about 2 ng/ml, or about 1.2 to about 1.6 ng/ml. Steady state is the point at which the amount of drug administered over a dosing interval equals the amount of drug being eliminated over that same period.

The hydrophilic implant comprising the octreotide formulation can be formed from a xerogel such that it readily absorbs water. In a hydrated state, the xerogel is referred to as a hydrogel. In either form, hydrated or unhydrated, it is biocompatible and non-toxic to the host and non-biodegradable. It is water-swellable and water-insoluble. When the hydrogel attains its maximum level of hydration, the water content of the hydrogel is referred to as "equilibrium water content" (EWC). The percent water content of the hydrogel (any state of hydration) is determined as follows:

$$\frac{\text{weight of hydrogel} - \text{weight of dry polymer(xerogel)}}{\text{weight of hydrogel}} \times 100$$

The hydrogel can be a homogeneous homopolymer or copolymer having a predetermined equilibrium water content (EWC) value formed by the polymerization of a mixture of ethylenically unsaturated monomer A and ethylenically unsaturated monomer B, for example, 2-hydroxyethyl methacrylate (HEMA) and hydroxypropyl methacrylate (HPMA). The predetermined EWC can be calculated by determining the EWC values of the hydrogel homopolymer of hydrophilic monomer A (homopolymer A) and the hydrogel homopolymer of hydrophilic monomer B (homopolymer B); determining the relationship of the EWC values of the homogeneous copolymers AB versus the chemical composition of said copolymers AB; selecting the targeted EWC value and determining the chemical composition of copolymer AB having the targeted EWC value; forming a polymerizable mixture of monomer A and monomer B in amounts sufficient to yield copolymer AB having the targeted EWC value; and effect the polymerization reaction to yield copolymer AB characterized by the targeted EWC value.

As used herein, "copolymer AB" or "copolymer AB consisting essentially of monomer A units and monomer B units" means that the addition copolymerization of monomer A and monomer B has been effected through the polymerizable ethylenic bond of the monomers. By way of illustration, if monomer A is 2-hydroxyethyl methacrylate and monomer B is N-methylacrylamide, copolymer AB contains recurring monomer A units and recurring monomer B units.

Unless the context indicates otherwise, the term "copolymer" includes polymers made by polymerizing a mixture of at least two ethylenically unsaturated monomers.

As used herein, "HEMA unit(s)" refer to a structure recurring in the polymer obtained by polymerizing hydrophilic material containing 2-hydroxyethyl methacrylate ("HEMA"). By the term "HEMA unit(s)" is meant the structure:

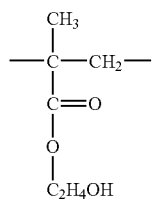

As used herein, "HPMA unit(s)" refers to a structure obtained by polymerizing hydrophilic material containing hydroxypropyl methacrylate ("HPMA"). By the term "HPMA unit(s)" is meant the structure:

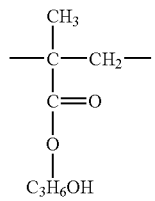

Liquid polymerizable material useful in the hydrophilic products include a wide variety of polymerizable hydrophilic, ethylenically unsaturated compounds, in particular, hydrophilic monomers such as, for example, the monoester of an acrylic acid or methacrylic acid with a polyhydroxy compound having an esterifiable hydroxyl group and at least one additional hydroxyl group such as, for example, the monoalkylene and polyalkylene polyols of methacrylic acid and acrylic acid, e.g., 2-hydroxyethyl methacrylate and acrylate, diethylene glycol methacrylate and acrylate, propylene glycol methacrylate and acrylate, dipropylene glycol methacrylate and acrylate, glycidyl methacrylate and acrylate, glyceryl methacrylate and acrylate, and the like; the 2-alkenamides, e.g., acrylamide, methacrylamide, and the like; the N-alkyl and N,N-dialkyl substituted acrylamides and methacrylamides such as N-methylmethacrylamide, N,N-dimethylmethacrylamide, and the like; N-vinylpyrrolidone; the alkyl-substituted N-vinylpyrrolidones, e.g., methyl substituted N-vinylpyrrolidone; N-vinylcaprolactam; the alkyl-substituted N-vinylcaprolactam, e.g., N-vinyl-2-methylcaprolactam, N-vinyl-3,5-dimethylcaprolactam, and the like. Acrylic and methacrylic acid can also be useful in these formulations.

Mixtures of hydrophilic monomers are employed in the polymerization reaction. The type and proportion of monomers are selected to yield a homogeneous polymer, preferably a crosslinked homogeneous polymer, which on hydration possesses the desired EWC value for the contemplated application or use. This value can be predetermined by preparing a series of copolymers using different monomer ratios, e.g., mixtures of HEMA and HPMA of varying ratios, ascertaining the EWC values of the copolymers, and plotting the relationship of % HPMA (or % HEMA) units in the HPMA/HEMA copolymers versus weight percent EWC of the copolymers (FIG. 1).

In some instances the polymerization of certain hydrophilic monomeric mixtures results in homogeneous hydrophilic copolymers that dissolve, to a varying extent, in an aqueous medium. In such cases, a small amount, e.g., up to 3 percent, of a copolymerizable polyethylenically unsaturated crosslinking agent, can be included in the monomeric mixture to obtain homogeneous crosslinked copolymers that are water-insoluble as well as water-swellable. Slightly crosslinked homopolymers of HEMA can have an EWC value of, for example, about 38%. Crosslinked copolymers of HEMA and HPMA have EWC values below about 38%. On the other hand, crosslinked copolymers of HEMA and acrylamide exhibit EWC values above 38% (w/v), e.g., upwards to approximately 75%, and higher. Therefore, depending on the useful or effective elution rate of the active compound, e.g., drug, that is required of a hydrogel delivery system for a particular application, one skilled in the art, by following the teachings disclosed herein, can tailor copolymer hydrogel membranes to elute the drug at a desired rate. Copolymers can contain, for example, about 15% to about 70% (weight) of HEMA units and from about 85 to 30% (weight) of units of a second ethylenic monomer and possess predetermined EWC values in the range of from about 20% to about 75%, preferably about 25%. Homogenous copolymers can include those made from hydrophilic monomeric mixtures containing from about 80% HPMA (weight), and from about 20% HEMA (weight). In further embodiments, the mixture can further contain a small amount of a polyethylenically unsaturated crosslinking agent, e.g., trimethylolpropane trimethacrylate ("TMPTMA").

Various aspects of the invention include homogeneous hydrophilic copolymers whose homogeneous polymer structure is formed by the polymerization of a mixture of hydrophilic monomers described previously; and the drug delivery device that utilizes the homogeneous polymer cartridges in the delivery system. The polymerization of a mixture of hydrophilic monomers and hydrophobic monomers yields heterogeneous polymers. Where hydrophobic segments are present in the polymer, the interfacial free energy increases, thus enhancing protein adsorption and mineralization after implantation in an animal. Hydrogels of poly-HEMA, for example, were measured to have interfacial free energy close to zero. According to the interfacial free energy interpretation, hydrogels of strictly hydrophilic components would strongly appear to be biocompatible with body tissue.

Slightly crosslinked poly-HEMA is a homogeneous, hydrophilic "homopolymer" (disregarding the relatively small quantities of polymerized crosslinking agent therein) of relatively fixed characteristics or values. Techniques for altering the "homopolymer" poly-HEMA to impart to it additional characteristics or properties are difficult, time-consuming, and oftentimes result in erratic property behavior. On the other hand, mixtures of HEMA with varying quantities of other polymerizable hydrophilic comonomer(s) can be polymerized to give predictable homogeneous hydrophilic copolymers having (predetermined) tailor-made properties.

Useful crosslinking agents that can be included in the polymerizable reaction medium include, for example, the polyethylenically unsaturated compounds having at least two polymerizable ethylenic sites, such as the di-, tri- and tetra-ethylenically unsaturated compounds, in particular, the tri-unsaturated crosslinking agents with/without the di-unsaturated crosslinking compounds, for example, divinylbenzene, ethylene glycol dimethacrylate and diacrylate, propylene glycol dimethacrylate and diacrylate; and the di-, tri- and tetra-acrylate or methacrylate esters of the following polyols: triethanolamine, glycerol, pentaerythritol, 1,1,1-trimethylolpropane and others.

The polymerization reaction can be carried out in bulk or with an inert solvent. Suitable solvents include, for example, water; organic solvents (e.g., water-soluble lower aliphatic monohydric alcohols as well as polyhydric alcohols, e.g., glycol, glycerine, dioxane, etc.; and mixtures thereof).

Compounds useful in the catalysis of the polymerizable ethylenically unsaturated compounds include the free-radical compounds and/or initiators of the type commonly used in vinyl polymerization such as the organic peroxides, percarbonates, hydrogen peroxides, and alkali metal sulfates. Illustrative examples include cumene hydroperoxide, t-butyl hydroperoxide, benzoyl peroxide, bis(4-t-butylcyclohexyl) peroxydicarbonate, hydrogen peroxide, 2,4-dichlorobenzoyl peroxide, acetyl peroxide, di-n-propyl peroxydicarbonate, di-t-butyl peroxide, di-sec-butyl peroxydicarbonate, ammonium sulfate, potassium sulfate, and sodium sulfate. A preferred catalyst is one that is effective at moderately low temperature such as, for example, at about 20-80° C. (e.g., tert-butyl peroctoate, benzoyl peroxide, and di(secbutyl) peroxydicarbonate).

A conventional redox polymerization catalyst can also be employed. Polymerization of the ethylenic compounds can be effected, for example, using radiation, e.g., ultraviolet, X-Ray, gamma radiation, microwave or other well-known forms of radiation. A preferred catalyst for ultraviolet cure is benzoin methyl ether. Catalysts and/or initiators and/or radiation are employed in a catalytically-effective amount to optimize the polymerization reaction.

The current invention focuses on the application of polyurethane based polymers, thermoplastics or thermosets, to the creation of implantable drug devices to deliver biologically active compounds at controlled rates for prolonged period of time. Polyurethane polymers are preferably made into cylindrical hollow tubes with one or two open ends through extrusion, (reaction) injection molding, compression molding, or spin-casting (see, e.g., U.S. Pat. Nos. 5,266,325 and 5,292,515, herein incorporated by reference in their entireties), depending on the type of polyurethane used.

Thermoplastic polyurethane can be processed through extrusion, injection molding or compression molding. Thermoset polyurethane can be processed through reaction injection molding, compression molding or spin-casting. The dimensions of the cylindrical hollow tube are determinable and can be adjusted precisely.

Polyurethane based polymers are synthesized from multi-functional polyols, isocyanates and chain extenders. The characteristics of each polyurethane can be attributed to its structure.

Thermoplastic polyurethanes are made of macrodiols, diisocyanates and difunctional chain extenders (e.g., U.S. Pat. Nos. 4,523,005 and 5,254,662, herein incorporated by reference in their entireties). Macrodiols make up the soft domains. Diisocyanates and chain extenders make up the hard domains. The hard domains serve as physical crosslinking sites for the polymers. Varying the ratio of these two domains can alter the physical characteristics of the polyurethanes.

Thermoset polyurethanes can be made of multifunctional (greater than difunctional) polyols and/or isocyanates and/or chain extenders (e.g., U.S. Pat. Nos. 4,386,039 and 4,131,604, herein incorporated by reference in their entireties). Thermoset polyurethanes can also be made by introducing unsaturated bonds in the polymer chains and appropriate crosslinkers and/or initiators to do the chemical crosslinking (e.g., U.S. Pat. No. 4,751,133, herein incorporated by reference in its entirety). By controlling the amounts of crosslinking sites and how they are distributed, the release rates of the actives can be controlled.

Different functional groups can be introduced into the polyurethane polymer chains through the modification of the backbones of polyols depending on the properties desired. Where the device is used for the delivery of water soluble drugs, hydrophilic pendant groups such as ionic, carboxyl, ether, and hydroxy groups are incorporated into the polyols to increase the hydrophilicity of the polymer (e.g., U.S. Pat. Nos. 4,743,673 and 5,354,835, herein incorporated by reference in their entireties). Where the device is used for the delivery of hydrophobic drugs, hydrophobic pendant groups such as alkyl, siloxane groups are incorporated into the polyols to increase the hydrophobicity of the polymer (e.g., U.S. Pat. No. 6,313,254, herein incorporated by reference in its entirety). The release rates of the actives can also be controlled by the hydrophilicity/hydrophobicity of the polyurethane polymers.

Small cylindrically-shaped implants of the invention can contain within their core, octreotide, preferably octreotide acetate, and optionally, a pharmaceutically acceptable carrier. The membrane thickness (between the interior and exterior surfaces) of the implant is substantially uniform, and serves as a rate-limiting barrier for the release of the contained agent. Such implants can be plasticized or hydrated and reshaped into other geometrically shaped articles for use in various medical applications.

In the manufacture of the implantable formulation, several factors can be considered. The release profile (delay time, release rate, and duration) is determined; the hydrophilic polymeric material is identified; and the diffusivity of the active agent through it (as a rate-limiting membrane) is measured. The hydration profile of the rate-limiting membrane for a given active agent may be readily determined by preparing a film of the selected polymer and subjecting it to a diffusion study, using a two compartment vertical glass cell, as is well known in the art.

The diffusion coefficient and the water content at which diffusion begins (below which substantially no diffusion occurs-hereinafter "% $H_d$") are determined. A series of membranes is prepared from various polymers. The membranes are then hydrated to their capacity and their EWCs are measured. The fully hydrated membranes are placed in the two-compartment, vertical glass cells to measure and the diffusion of the macromolecular composition through the membrane materials at the various EWCs is plotted. The equilibrium water content of the most hydrated membrane through which no diffusion is detected (e.g., none of the active agent diffuses into the receptor cell) is the % $H_d$ for the system being tested. This can be accomplished by plotting a curve of the permeability versus EWC.

The permeability results (diffusion coefficients) are obtained according to Fick's First Law of Diffusion, by use of the equation:

$$\frac{dQ}{dt} = \frac{APC_d}{1}$$

wherein dQ/dt is the flux through the membrane material (μg/hr); it is measured as the slope of the linear part of the curve of cumulative transport versus time; wherein A is the area of the membrane (cm$^2$); wherein P is the membrane's permeability coefficient (cm$^2$/hr), or $DK_d$, wherein D is the diffusivity of the membrane (cm$^2$/hr), and $K_d$ is the partition coefficient for the membrane/donor solution; wherein 1 is the membrane thickness as measured at the end of the experiment (cm); and wherein $C_d$ is the concentration of the donor solution (μg/cm$^3$).

The release delay profile can then be determined. Another series of polymeric membranes can be prepared, again varying the amounts of crosslinker and monomers. These membranes are then hydrated, but only partially, e.g., to a water content less than or equal to % $H_d$. The partially hydrated membranes are placed in two-compartment vertical glass cells to measure and plot the diffusion of the active compound through the membranes versus time. Buffer solutions for the donor and receptor cells can be selected to contact the partially-hydrated membranes and further hydrate them at approximately the same rate at which they will hydrate in the delivery environment. The time between commencement of the diffusion study, i.e., addition of the active agent to the donor cell, and the detection of a pharmaceutically-effective concentration of the active agent in the receptor cell is the release delay time for that combination of polymer and initial percent hydration.

To determine the physical dimensions of the cylindrically-shaped device, the total amount of active agent to be delivered is determined. This is the product of the desired daily dosage and the duration of delivery. In preferred embodiments, the duration of delivery is at least about 2 months, more preferably about 6 months, and up to about two years. The desired daily dosage is, for example, about 10 to about 1000 μg of octreotide per day, preferably about 20 to about 800 μg of octreotide per day, more preferably about 30 to about 300 μg of octreotide per day.

The volume of the cylindrical reservoir (core) of a cylindrically-shaped device is equal to $\Pi r_i^2 h$ wherein $r_i$ is the radius of the reservoir and h is its height.

The formula for steady state release from a cylinder is:

$$[dQ/dt] = [2\Pi h DK_d C_d]/[ln(r_o/r_i)]$$

wherein $r_o$ is the outside radius of the cylindrical device; and wherein $C_d$ is the concentration of drug in the donor solution, i.e., the carrier. Steady state release is obtained when $C_d$ is maintained at saturation. The thickness of the membrane needed for the desired sustained release is, therefore, $r_o-r_i$.

The amount of active agent employed will depend not only on the desired daily dose but also on the number of days that dose level is to be maintained. While this amount can be calculated empirically, the actual dose delivered is a function of any interaction with materials and the carrier, if employed in the device.

Once the appropriate polyurethane polymer is chosen, the best method to fabricate the cylindrically shaped implants can be determined by one of skill in the art to achieve suitable delivery characteristics as described herein.

For thermoplastic polyurethanes, precision extrusion and injection molding are can be used to produce two open-end hollow tubes with consistent physical dimensions. The reservoir can be loaded freely with appropriate formulations containing actives and carriers or filled with pre-fabricated pellets to maximize the loading of the actives. To seal the two open ends, two pre-fabricated end plugs can be used. The sealing step can be accomplished through the application of heat or solvent or any other means to seal the ends, preferably permanently.

For thermoset polyurethanes, precision reaction injection molding or spin casting is the preferred choice depending on the curing mechanism. Reaction injection molding is used if the curing mechanism is carried out through heat and spin casting is used if the curing mechanism is carried out through light and/or heat. Preferably, hollow tubes with one open end are made by spin casting. Preferably, hollow tubes with two open ends are made by reaction injection molding. The reservoir can be loaded in the same way as the thermoplastic polyurethanes.

Preferably, to seal an open end, an appropriate light-initiated and/or heat-initiated thermoset polyurethane formulation is used to fill the open end and this is cured with light and/or heat. More preferably, a pre-fabricated end plug can also be used to seal the open end by applying an appropriate light-initiated and/or heat-initiated thermoset polyurethane formulation on to the interface between the pre-fabricated end plug and the open end and cured it with the light and/or heat or any other means to seal the ends, preferably permanently. The solid active agent and optional carriers can be compressed into pellet form to maximize the loading of the actives.

Prior to implantation, the implantable formulations can be optionally hydrated or "primed" for a predetermined period of time. Priming can enable the active ingredient to begin to infiltrate and saturate the walls of the hydrogel and potentially begin to leach out of the hydrogel prior to implantation depending upon the amount of time the implant is primed. A primed implant will begin to release active ingredient substantially upon implantation, and may result in a peak release of the drug shortly after implantation. In contrast, little to no priming may result in substantially no release of the active ingredient upon implantation for a period of time until the implant becomes hydrated and the active ingredient begins to be released, however these priming characteristics depend on the specific formulations being used. The invention is directed to, for example, a method of administering a controlled-release octreotide formulation comprising implanting a dehydrated octreotide formulation into a subject.

Depending upon the types of active ingredient, hydrophilic or hydrophobic, the appropriate conditioning and priming media will be chosen. Water based media are preferred for hydrophilic actives and oil based media are preferred for hydrophobic actives. Alternatively, certain implants of the invention do not need to be primed prior to implantation. In some instances, priming will improve delivery of the active agent in a controlled fashion, but in other instances, priming prior to implantation in a subject will not affect delivery in a way to justify the added time and hassle required for priming the implant.

The hydrating liquid useful in the practice of the invention is typically a liquid simulating the environment in which the active compound will be released, e.g., body fluid, sterile water, tear fluid, physiological saline solution, phosphate buffer solution and the like. While liquids other than water are useful as the hydrating liquid, the degree to which a hydrophilic membrane is hydrated is referred to as its "water content."

The priming and conditioning of the drug delivery devices involves the loading of the actives (drug) into the polymer that surrounds the reservoir, and thus prevent loss of the active before the actual use of the implant. The conditions used for the conditioning and priming step depend on the active agent, the temperature and the medium in which they are carried out. The conditions for the conditioning and priming can be the same in some instances.

The conditioning and priming step in the process of the preparation of the drug delivery devices is performed to obtain a determined rate of release of a specific drug. The conditioning and priming step of the implant containing a hydrophilic drug is preferably carried out in an aqueous medium, more preferably in a saline solution. For hydrophobic drugs, the medium can be a plasma-like medium, including, but not limited to, cyclodextrin. The conditioning and priming steps are carried out by controlling three specific factors, namely the temperature, the medium and the period of time.

A person skilled in the art would understand that the conditioning and priming step of the drug delivery device will be affected by the medium in which the device is placed. Histrelin and naltrexone implants, for example, can be conditioned and primed in saline solution, more specifically, conditioned in saline solution of 0.9% sodium content and primed in saline solution of 1.8% sodium chloride content.

The temperature used to condition and prime the drug delivery device can vary across a wide range of temperatures, but, in some instances 37° C., is used.

The time period used for the conditioning and priming of the drug delivery devices can vary from about a single day to several weeks depending on the release rate desired for the specific implant or drug.

A person skilled in the art will understand that the steps of conditioning and priming the implants, where appropriate or necessary, is to optimize the rate of release of the drug contained within the implant. As such, a shorter time period spent on the conditioning and the priming of a drug delivery device can result, for example, in a lower rate of release of the drug compared to a similar drug delivery device that has undergone a longer conditioning and priming step. Without priming, however, it was unexpectedly found that effective release occurred over a longer period of time (e.g., 28 weeks and beyond), and lower serum concentrations of the active ingredient were found to have ameliorative effects.

The temperature in the conditioning and priming step can also affect the rate of release in that a lower temperature results in a lower rate of release of the drug contained in the drug delivery device when compared to a similar drug delivery device that has undergone a treatment at a higher temperature.

Similarly, in the case of aqueous solutions, which are in some cases preferably saline solutions, the sodium chloride content of the solution will also determine what type of rate of release will be obtained for the drug delivery device. More specifically, a lower content of sodium chloride can result in a higher rate of release of drug when compared to a drug delivery device that has undergone a conditioning and priming step where the sodium chloride content was higher.

To identify the location of the implant, radiopaque material can be incorporated into the delivery device by inserting it into the reservoir or by making it into end plug to be used to seal the cartridge.

The formulation of the present invention can contain a pharmaceutically acceptable carrier that can include, for example, suspending media, solvents, aqueous systems and solid substrates or matrices.

Suspending media and solvents useful as the carrier include, for example, oils such as silicone oil (particularly medical grade), corn oil, castor oil, peanut oil and sesame oil; condensation products of castor oil and ethylene oxide; liquid glyceryl triesters of a lower molecular weight fatty acid; lower alkanols; glycols; and polyalkylene glycols.

The aqueous systems include, for example, sterile water, saline, dextrose, dextrose in water or saline, and the like. The presence of electrolytes in the aqueous systems may tend to lower the solubility of the macromolecular drug in them.

The solid substrates or matrices include, for example, starch, gelatin, sugars (e.g., glucose), natural gums (e.g., acacia, sodium alginate, carboxymethyl cellulose), and the like. In a preferred embodiment, the pharmaceutical formulation further comprises about 2% to about 20%, more preferably about 10% hydroxypropylcellulose. In addition, the pharmaceutical formulations may also contain hydroxyporopylcellulose, hydroxyethyl cellulose, methyl cellulose, sodium carboxymethyl cellulose, modified starch or crosslinked polyvinyl pyrrolidone.

The carrier can also contain adjuvants such as preserving, stabilizing, wetting and emulsifying agents and the like.

In one embodiment, a pharmaceutical formulation of the present invention comprises a formulation of octreotide acetate within a mixture of HEMA and HPMA copolymer, preferably about 20% HEMA and about 80% HPMA. The pharmaceutical formulation can comprise, for example, about 20 to about 150 milligrams of octreotide, preferably about 40 to about 90 milligrams. The formulation can further comprise between about 2 to about 20% excipients. The formulation can also contain about 10% hydroxypropylcellulose and/or about 2% magnesium stearate.

A pharmaceutical formulation of the present invention can comprise a formulation of about 50 milligrams of octreotide within a mixture of HEMA and HPMA copolymer, preferably about 20% HEMA and about 80% HPMA. In a further embodiment, the formulation further comprises about 10% hydroxypropylcellulose and 2% magnesium stearate with the octreotide acetate.

A pharmaceutical formulation of the present invention also can comprise a formulation of about 83 mg of octreotide within a mixture of HEMA and HPMA copolymer, preferably about 40% HEMA and about 60% HPMA. In a further embodiment, the formulation further comprises about 10% hydroxypropylcellulose and 2% magnesium stearate with the octreotide acetate. The pharmaceutical formulations may also contain stearic acid, vegetable stearin, talc and silica.

A pharmaceutical formulation of the present invention can also comprise a formulation of about 20 milligrams to about 150 milligrams, more preferably about 40 milligrams to about 90 milligrams, of octreotide in a xerogel, preferably a hydrogel or a polyurethane based polymer.

A method of treating a disease associated with a hormonal disorder is provided. The method can include administering octreotide and maintaining a plasma concentration at steady state of octreotide between about 0.1 ng/ml and about 9 ng/ml over an extended period of time, preferably at least about two months, and more preferably about six months and up to about two years. In preferred embodiment, the plasma concentration at steady state of octreotide is maintained between about 1 ng/ml and about 2 ng/ml, more preferably about 1.2 ng/ml to about 1.6 ng/ml, over an extended period of time. Hormonal disorders include, for example, acromegaly.

The invention is also directed to methods for decreasing GH levels by administering octreotide and maintaining a steady state plasma concentration of octreotide between about 0.1 ng/ml and about 9 ng/ml, about 0.5 ng/ml to about 1 ng/ml, about 1 ng/ml to about 2 ng/ml, or about 1.2 to about 1.6 ng/ml, over an extended period of time, preferably at least about two months, and more preferably about six months, and up to about two years.

The invention is also directed to methods for decreasing IGF-1 levels by administering octreotide and maintaining a plasma concentration of octreotide between about 0.1 ng/ml and about 9 ng/ml, about 0.5 ng/ml to about 1 ng/ml, about 1 ng/ml to about 2 ng/ml, or about 1.2 to about 1.6 ng/ml, over an extended period of time, preferably at least about two months, and more preferably about six months, and up to about two years.

The invention is further directed to methods of treating acromegaly comprising administering at least one implant of the present invention, preferably two implants, of the present invention. In the method, each implant administered can contain between about 20 to about 150 milligrams of octreotide, preferably about 40 to about 90 milligrams of octreotide, more preferably about 50 milligrams of octreotide, and release a therapeutically effective amount of octreotide over a period of at least two months, preferably about six months, and up to about two years.

The invention is further directed to methods of treating symptoms associated with carcinoid tumors and VIPomas. Methods of treating severe diarrhea and flushing episodes associated with carcinoid tumors by administering an implantable formulation of octreotide, which releases a therapeutically effective amount of octreotide over at least about two months, preferably about six months and up to about two years, are also encompassed by the present invention. Methods of treating watery diarrhea associated with VIPomas by administering an implantable formulation of octreotide, which release a therapeutically effective amount of octreotide over at least about two months, preferably about six months and up to about two years, are also encompassed by the present invention.

The formulations of the present invention exhibit a specific, desired release profile that maximizes the therapeutic effect while minimizing adverse side effects of the implant. The desired release profile can be described in terms of the maximum plasma concentration of the drug or active agent (Cmax) and the plasma concentration of the drug or active agent at steady state (Css).

The present invention is also directed to therapeutic compositions of a hydrogel and octreotide, wherein, upon implantation, the octreotide is released at a rate that provides and/or maintains a Css of about 0.1 ng/ml to about 9 ng/ml, about 0.5 ng/ml to about 1 ng/ml, about 1 ng/ml to about 2 ng/ml, or about 1.2 ng/ml to about 1.6 ng/ml. A further embodiment is a therapeutic composition of a hydrogel and octreotide, wherein, upon implantation, the octreotide is released at a rate of from about 10 µg to about 1000 µg per day over an extended period of time, preferably about 20 µg to about 800 µg, more preferably about 30 µg to about 300 µg per day. The octreotide can be release over at least about two months, about six months, or up to about two years. The hydrogel can comprise methacrylate based polymers or polyurethane based polymers.

Another embodiment is a controlled-release formulation comprising octreotide and a hydrophilic polymer, which permits release of the octreotide at a rate of about 30 µg to about 250 µg per day over at least about two months, about six months or about two years in vitro. In some embodiment, delivery is about 100 µg to about 130 µg per day. In a further embodiment, the hydrophilic polymer of the formulation permits release of octreotide at an average rate of about 100 µg per day in vitro. The hydrophilic polymer can be selected from polyurethane based polymers and methacrylate based polymers.

A further embodiment of the present invention is a controlled-release formulation comprising octreotide for implantation, wherein the formulation comprises octreotide in a hydrophilic polymer effective to permit in vitro release of no more than about 20% of said octreotide from the formulation after about 6 weeks; and about 60% of said octreotide from said formulation after about six months.

The amount of a pharmaceutically-acceptable octreotide (e.g., various salts, salvation states, or prodrugs thereof) included in the pharmaceutical composition of the present invention will vary depending upon a variety of factors, including, for example, the specific octreotide used, the desired dosage level, the type and amount of hydrogel used, and the presence, types and amounts of additional materials included in the composition. The amount of octreotide, or a derivative thereof, in the formulation varies depending on the desired dose for efficient drug delivery, the molecular weight, and the activity of the compound. The actual amount of the used drug can depend on a patient's age, weight, sex, medical condition, disease or any other medical criteria. The actual drug amount is determined according to intended medical use by techniques known in the art. The pharmaceutical dosage formulated according to the invention can be administered, for example, about once every six months as determined by the attending physician.

The octreotide typically is formulated in the implant or other pharmaceutical composition in amounts of about 20 milligrams to about 150 milligrams, preferably about 40 to about 90 milligrams of octreotide, more preferably about 50 to about 85 milligrams. For adults, the daily dose for treatment of acromegaly is typically about 300 µg to about 600 µg of immediate release octreotide per day (100 µg or 200 µg Sandostatin®). The amount of octreotide in the composition can be selected, for example, to release from about 10 µg to about 1000 µg per day over an extended period of time, about 20 µg to about 800 µg per day, or about 30 µg to about 300 µg per day. Such release rates maintain desired therapeutic levels in a patient's blood at about 0.1 to about 9 ng/ml over an extended period of time.

The hydrogel device in which octreotide is contained provides a controlled-release of octreotide into the plasma of the patient. Hydrogels suitable for controlling the release rate of octreotide for use in the pharmaceutical compositions of the present invention include polymers of hydrophilic monomers, including, but not limited to HPMA, HEMA and the like. Such hydrogels are also capable of preventing degradation and loss of octreotide from the composition.

IA pharmaceutical formulation of the present invention can comprise octreotide acetate within a hydrophilic copolymer of 2-hydroxyethyl methacrylate and hydroxypropyl methacrylate. The copolymer of the pharmaceutical formulation can comprise, for example, about 20% HEMA and about 80% HPMA. The copolymer of the pharmaceutical formulation can alternatively comprise, for example, about 40% HEMA and about 60% HPMA.

The size, shape and surface area of the implant can be modified to increase or decrease the release rate of octreotide from the implant.

The pharmaceutical composition of the present invention can include also auxiliary agents or excipients, for example, glidants, dissolution agents, surfactants, diluents, binders including low temperature melting binders, disintegrants and/or lubricants. Dissolution agents increase the dissolution rate of octreotide from the dosage formulation and can function by increasing the solubility of octreotide. Suitable dissolution agents include, for example, organic acids such as citric acid, fumaric acid, tartaric acid, succinic acid, ascorbic acid, acetic acid, malic acid, glutaric acid and adipic acid, which can be used alone or in combination. These agents man also be combined with salts of the acids, e.g., sodium citrate with citric acid, to produce a buffer system.

Other agents that can alter the pH of the microenvironment on dissolution and establishment of a therapeutically-effective plasma concentration profile of octreotide include salts of inorganic acids and magnesium hydroxide. Other agents that can be used are surfactants and other solubilizing materials. Surfactants that are suitable for use in the pharmaceutical composition of the present invention include, for example, sodium lauryl sulfate, polyethylene stearates, polyethylene sorbitan fatty acid esters, polyoxyethylene castor oil derivatives, polyoxyethylene alkyl ethers, benzyl benzoate, cetrimide, cetyl alcohol, docusate sodium, glyceryl monooleate, glyceryl monostearate, glyceryl palmitostearate, lecithin, medium chain triglycerides, monoethanolamine, oleic acid, poloxamers, polyvinyl alcohol and sorbitan fatty acid esters.

Diluents that are suitable for use in the pharmaceutical composition of the present invention include, for example, pharmaceutically acceptable inert fillers such as microcrystalline cellulose, lactose, sucrose, fructose, glucose dextrose, or other sugars, dibasic calcium phosphate, calcium sulfate, cellulose, ethylcellulose, cellulose derivatives, kaolin, mannitol, lactitol, maltitol, xylitol, sorbitol, or other sugar alcohols, dry starch, saccharides, dextrin, maltodextrin or other polysaccharides, inositol or mixtures thereof. The diluent can be a water-soluble diluent. Examples of diluents include, for example: microcrystalline cellulose such as Avicel PH112, Avicel PH101 and Avicel PH102 available from FMC Corporation; lactose such as lactose monohydrate, lactose anhydrous, and Pharmatose DCL 21; dibasic calcium phosphate such as Emcompress available from Penwest Pharmaceuticals; mannitol; starch; sorbitol; sucrose; and glucose. Diluents are carefully selected to match the specific composition with attention paid to the compression properties. The diluent is preferably used in an amount of about 2% to about 80% by weight, preferably about 20% to about 50% by weight, of the controlled-release composition.

Glidants are used to improve the flow and compressibility of ingredients during processing. Suitable glidants include, for example, colloidal silicon dioxide, a sub-micron fumed silica that can be prepared, for example, by vapor-phase hydrolysis of a silicon compound such as, for example, silicon tetrachloride. Colloidal silicon dioxide is a sub-micron amorphous powder that is commercially available from a number of sources, including Cabot Corporation (under the trade name Cab-O-Sil®); Degussa, Inc. (under the trade name Aerosil®); and E.I. DuPont & Co. Colloidal silicon dioxide is also known as colloidal silica, fumed silica, light anhydrous silicic acid, silicic anhydride and silicon dioxide fumed, among others. In one embodiment, the glidant comprises Aerosil® 200.

Disintegrants that are suitable for use in the pharmaceutical composition of the present invention include, for example, starches, sodium starch glycolate, crospovidone, croscarmellose, microcrystalline cellulose, low substituted hydroxypropyl cellulose, pectins, potassium methacrylate-divinylbenzene copolymer, poly(vinyl alcohol), thylamide, sodium bicarbonate, sodium carbonate, starch derivatives, dextrin, beta cyclodextrin, dextrin derivatives, magnesium oxide, clays, bentonite and mixtures thereof.

The active ingredient of the present invention can be mixed with excipients that are pharmaceutically-acceptable and compatible with the active ingredient and in amounts suitable for use in the therapeutic methods described herein. Various excipients can be homogeneously mixed with octreotide of the present invention as would be known to those skilled in the art. Octreotide, for example, can be mixed or combined with excipients such as but not limited to microcrystalline cellulose, colloidal silicon dioxide, lactose, starch, sorbitol, cyclodextrin and combinations of these.

Lubricants that are suitable for use in the pharmaceutical composition of the present invention include agents that act on the flowability of the powder to be compressed include but are not limited to silicon dioxide such as, for example, Aerosil® 200, talc; stearic acid, magnesium stearate, calcium stearate, hydrogenated vegetable oils, sodium benzoate, sodium chloride, leucine carbowax, magnesium lauryl sulfate, and glyceryl monostearate.

The invention is further directed to a controlled-release implantable dosage formulation that includes an effective amount a octreotide in a hydrogel, and that, upon administration to a patient or as part of a therapy regimen, provides a release profile (of therapeutically-effective blood plasma level of octreotide) extending for a period of at least about two months, about six months or up to about two years.

The dosage formulation of the present invention can comprise one or more pharmaceutically-acceptable excipients. In preferred embodiments, the dosage formulation will comprise diluents and a lubricant in addition to octreotide unit dose and the rate-controlling polymer. For this purpose, magnesium stearate is a suitable excipient. When these materials are used, the magnesium stearate component can comprise from about 0.5 to about 5% w/w of the dosage formulation (e.g., about 2%), and the hydrogel and octreotide comprise the remainder of the formulation.

Another suitable excipient is hydroxypropylcellulose. When used, the hydroxypropylcellulose component can comprise from about 0.5 to about 20% w/w of the dosage formulation (e.g., about 10%), and the hydrogel and octreotide comprise the remainder of the formulation.

In one embodiment, the formulation comprises both magnesium stearate and hydroxypropylcellulose, preferably about 2% magnesium stearate and about 10% hydroxypropylcellulose and the hydrogel and octreotide comprise the remainder of the formulation.

The compositions of the present invention can be used for the treatment of hormonal diseases, e.g., acromegaly, or symptoms thereof characterized by increased levels of GH and IGF-1 by administering to a patient an implantable formulation of the present invention. The implant can be administered, for example, every about six months, and release a therapeutically-effective amount of octreotide. The implantable composition releases a concentration of octreotide in the patient at about the minimum therapeutically-effective level to ameliorate the hormonal disorder, yet relatively lower compared to the maximum concentration to enhance restful periods for the patient during the day. The compositions can be administered to a subject at a dose and for a period sufficient to allow the subject to tolerate the dose without showing adverse effects and thereafter increasing the dose of the active agent, if needed, at selected intervals of time until a therapeutic dose is achieved in the subject. The active agent can be administered, for example, at a dose of from about 10 µg to about 1000 µg, about 20 µg to about 800 µg, or about 30 µg to about 300 µg, of octreotide daily for a period of at least about two months, about six months, or up to about two years.

Compositions of the present invention where the octreotide is octreotide acetate are suitable for use in the treatment of hormonal disorders that are characterized by increased levels of GH and IGF-1, e.g., acromegaly. The octreotide acetate agent in accordance with the invention is also suitable for the treatment of symptoms associated with carcinoid syndrome and VIPomas.

Additional features and embodiments of the present invention are illustrated by the following non-limiting examples.

EXEMPLIFICATION

Example 1

In Vitro Octreotide Release Rates

This example illustrates preparation of implantable octreotide formulations of the present invention and their in vitro release of octreotide. In the present study, a series of implants were tested to determine stability and in vitro release characteristics of octreotide from the hydrogel formulations over about 22 weeks (No. 146), 28 weeks (No. 136) and 33 weeks (all other formulations). Each implant contained about 50 milligrams of octreotide acetate and about 2% stearic acid, but the polymer cartridges contained different amounts of HEMA and HPMA and therefore exhibited different % EWCs, as depicted in Table 1.

TABLE 1

| Formulation Number | % HEMA | % HPMA | % EWC | Excipients/Other Ingredients |
|---|---|---|---|---|
| 146 | 0 | 99.5 | 22.9 | 2% stearic acid |
| 145 | 10 | 89.5 | 23.4 | 2% stearic acid |
| 147 | 15 | 84.5 | 24.4 | 2% stearic acid |
| 133 | 20 | 79.5 | 25.2 | 2% stearic acid |
| 144 | 25 | 74.5 | 25.6 | 2% stearic acid |
| 143 | 30 | 69.5 | 26.1 | 2% stearic acid |
| 142 | 35 | 64.5 | 26.6 | 2% stearic acid |
| 136 | 40 | 59.5 | 27.6 | 2% stearic acid |

Figure 2:
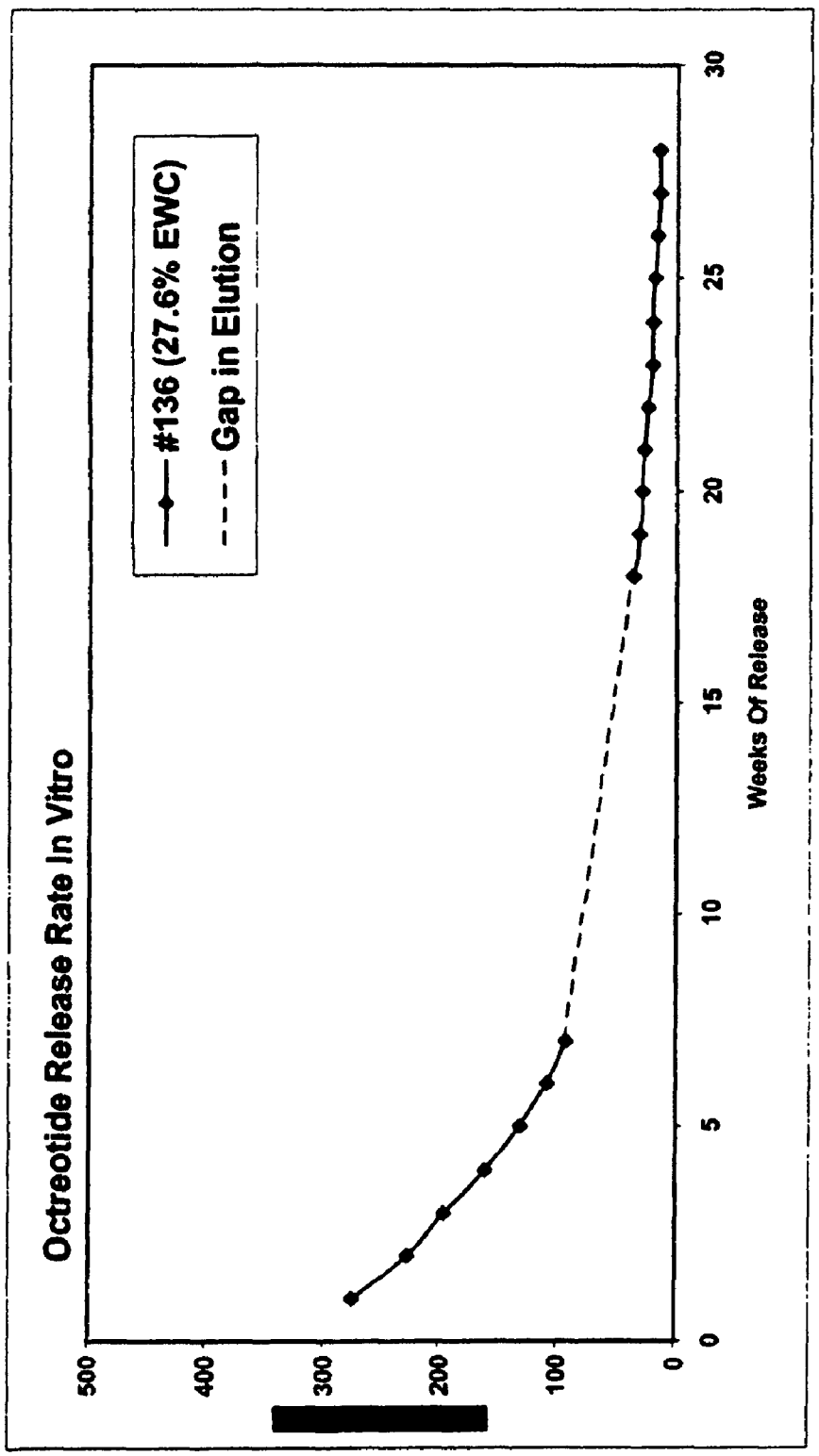
FIG. 2 is a graph showing the release of octreotide from an implant formulation of the present invention.
Figure 3:
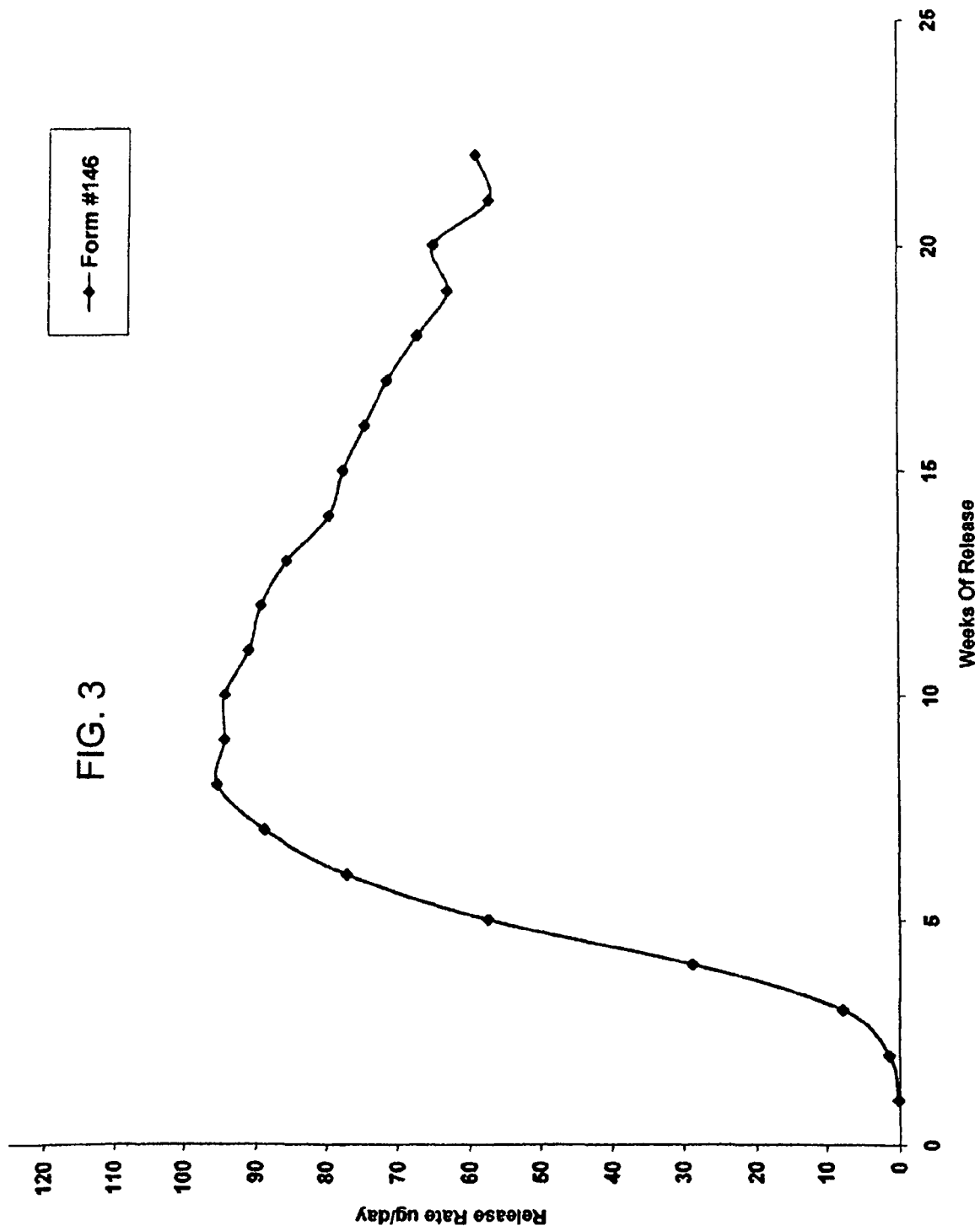
FIG. 3 is a graph showing the release of octreotide from an implant formulation of the present invention.
Figure 4:
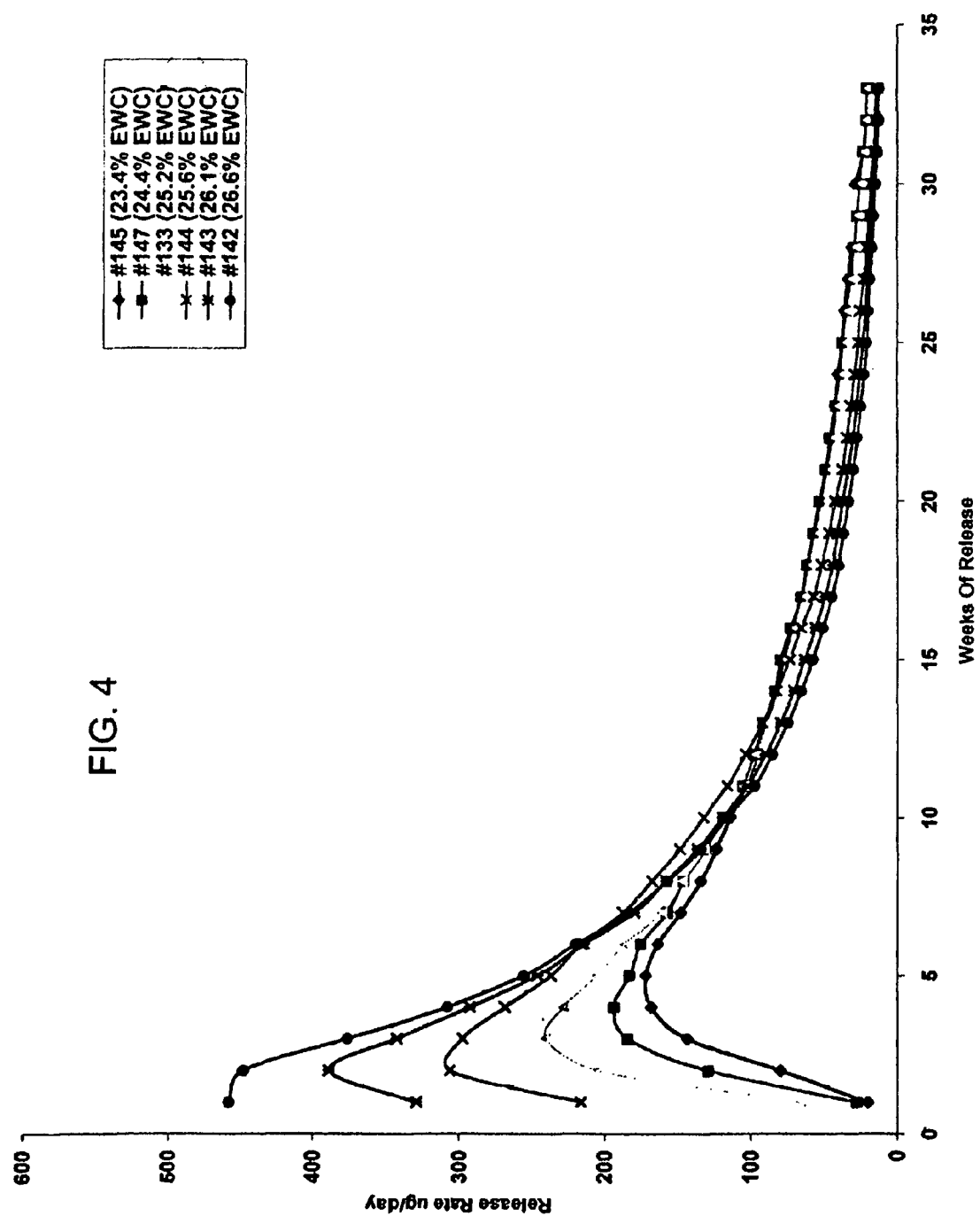
FIG. 4 is a graph showing the release of octreotide from six different implant formulations of the present invention.

FIGS. 2, 3 and 4 depict the release of octreotide from the implant per day for each of the formulations provided above. As noted in FIG. 2, the initial release was relatively high and dropped relatively quickly for Formulation No. 136. As shown in FIG. 3, the initial release rate for Formulation No. 146 was relatively low. FIG. 4 presents the release profiles for Formulation Nos: 145, 147, 133, 144, 143 and 142. As shown in FIG. 4, the initial release rates show a good relationship with the % EWC, ranging from 20 to 450 µg per day for % EWCs of 22.9 to 27.6%. Problems were encountered, however, with respect to the osmotic pressure differential within the implant and the elution media. To stabilize the octreotide formulations, a number of experiments were designed using excipients that would provide better stability based on a "preferential hydration" principle.

Example 2

Formulation Study in Calf Serum

To determine the effect of osmotic pressure on the swelling problem two implants of the present invention corresponding to Formulation No. 136 and Formulation No. 143 were eluted in calf serum. In particular, Formulation No. 136, composed of about 40% HEMA and 60% HPMA, containing octreotide acetate with 2% stearic acid and Formulation No. 143, composed of about 30% HEMA and 70% HPMA, containing a mixture of 20% PEG3300 and 80% octreotide acetate, were tested. After three months, the implants exhibited normal appearance, being relatively straight and only slightly swollen.

Example 3

Formulation Study

Due to osmotic pressure differential, the implants described in Example 1 were seen to swell significantly-ultimately resulting in bursting of the implants. This example illustrates formulations designed to screen agents useful in stabilization of the octreotide implant. A series of implants was monitored to determine the effect of excipient on implant shape and durability. Each of the polymer cartridges was composed of about 28% HEMA, about 66.5% HPMA and 5% glycerin. The contents contained octreotide acetate with various excipients, as shown in Table 2.

TABLE 2

| Sample No. | Excipients/Other Ingredients |
|---|---|
| 1 | None |
| 2 | 20% PEG 3300 |
| 3 | 40% PEG 3300 |
| 4 | 2% Stearic acid (control) |
| 5 | 10% Glycolic acid |
| 6 | 20% Poly(lactic acid) |
| 7 | 10% Mannitol |
| 8 | 10% MCC (microcrystalline cellulose) |
| 9 | 20% MCC |
| 10 | 10% Sesame oil |

Hydrophobic agents such as sesame oil and MCC separated in the formulation and did not provide "preferential hydration" and were less preferable in accordance with the present invention. Hydrophilic agents like PEG 3300 increased the osmotic pressure differential and increased swelling. Low molecular weight additives like mannitol and glycolic acid did not provide a stabilizing effect and resulted in a decrease in integrity. None of these agents provided satisfactory stabilization of the octreotide formulations.

Example 4

Formulation Study and In Vitro Octreotide Release Rates

This study was conducted to evaluate stability of octreotide in hydrogel implants using various excipients as shown in Table 3. The excipients were chosen to have high molecular weight and some hydrophilic nature. Each implant was made from polymer cartridges composed of about 20% HEMA and about 80% HPMA. The appearance of the implants in saline was monitored and rated over the course of nine weeks. The results are shown in Table 3.

TABLE 3

| Formulation No. | Excipients/Other Ingredients | Implant Appearance at 9 Weeks (see key below) |
|---|---|---|
| 133 | 20% Dextran | 3 |
| 133 | 20% TPGS (vitamin E derivative) | 2 |
| 133 | 20% HEC (hydroxyethyl cellulose) | 3 |
| 133 | 20% HPC (hydroxypropyl cellulose) | 2 |
| 133 | 20% Albumin | 2 |
| 133 | 20% Pectin | 2 |
| 133 | 20% AcDiSol | 1.5 |
| 133 | 20% Carbopol | 1 |
| 133 | 2% SA (stearic acid) - control | 4 |

Figure 5:
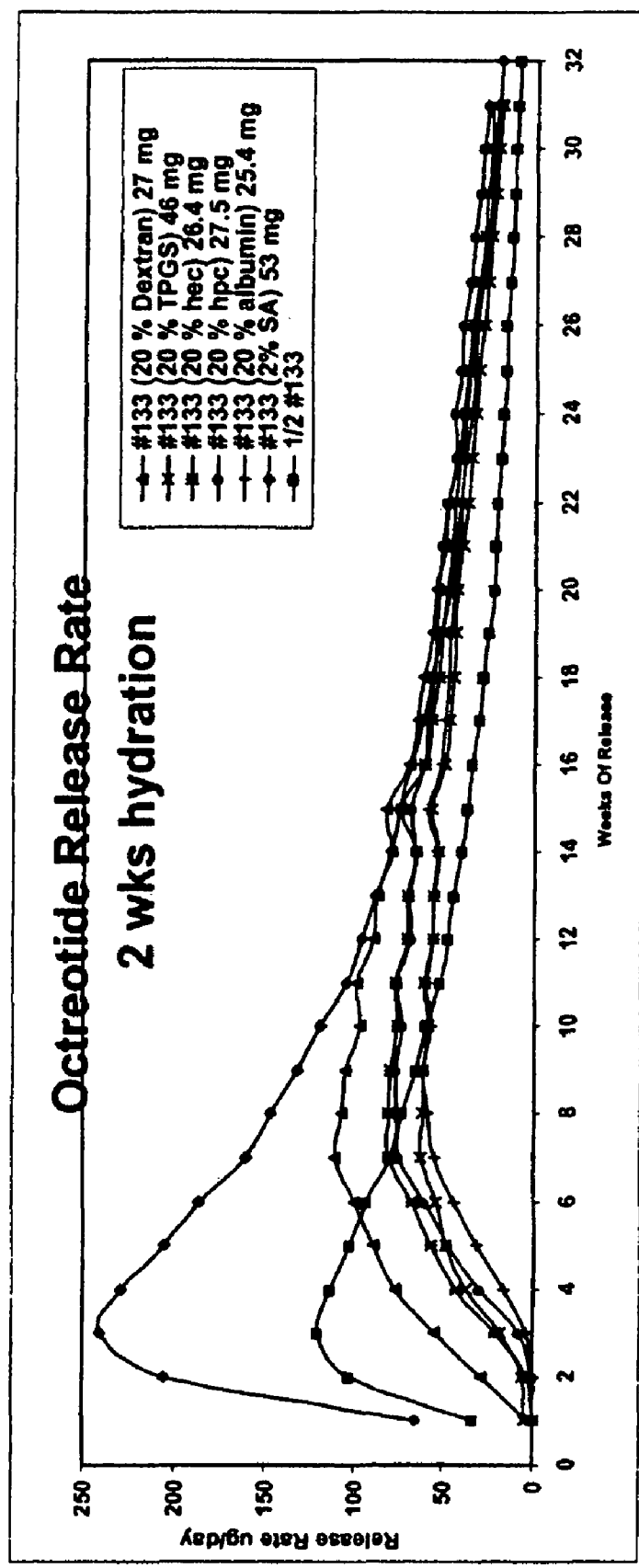
FIG. 5 is a graph showing the release of octreotide from different implant formulations of the present invention.

As depicted in FIG. 5, the formulation containing dextran had the highest elution rate. The formulations containing pectin, AcDiSol and Carbopol exhibited less than satisfactory release after two weeks hydration and nine weeks elution. Accordingly, a preferred embodiment having superior stabilizing effect, combination of good elution and appearance, was achieved with hydroxypropylcellulose.

Example 5

One-Month Implantation Study in a Healthy Dog

This example illustrates preparation of formulations of the present invention and their release of octreotide or pharmaceutically-acceptable salts thereof. A healthy dog was implanted with one octreotide subdermal implant of the present invention. The octreotide subdermal implant formulation had a water content of 26.6%, containing 44 mg octreotide acetate. In vitro release rates were estimated at about 500 μg/day in week 1 and decreasing to about 300 μg/day in week 4 for a total release of about 10 mg of octreotide over the duration of the study. The implant was removed at 28 days after implantation. The implant used in this study was about 3.5 cm in length. Blood samples (1.5 ml) to obtain the serum concentration of octreotide acetate, IGF-1 and GH were obtained on days 0, 1-7, 11, 14, 18, 21, 25 and 28 by jugular puncture without anesthesia and without fasting. Clinical observations included that the octreotide implant formulation was well-tolerated, food intake was normal, and no abnormal behavior was noted.

Figure 6:
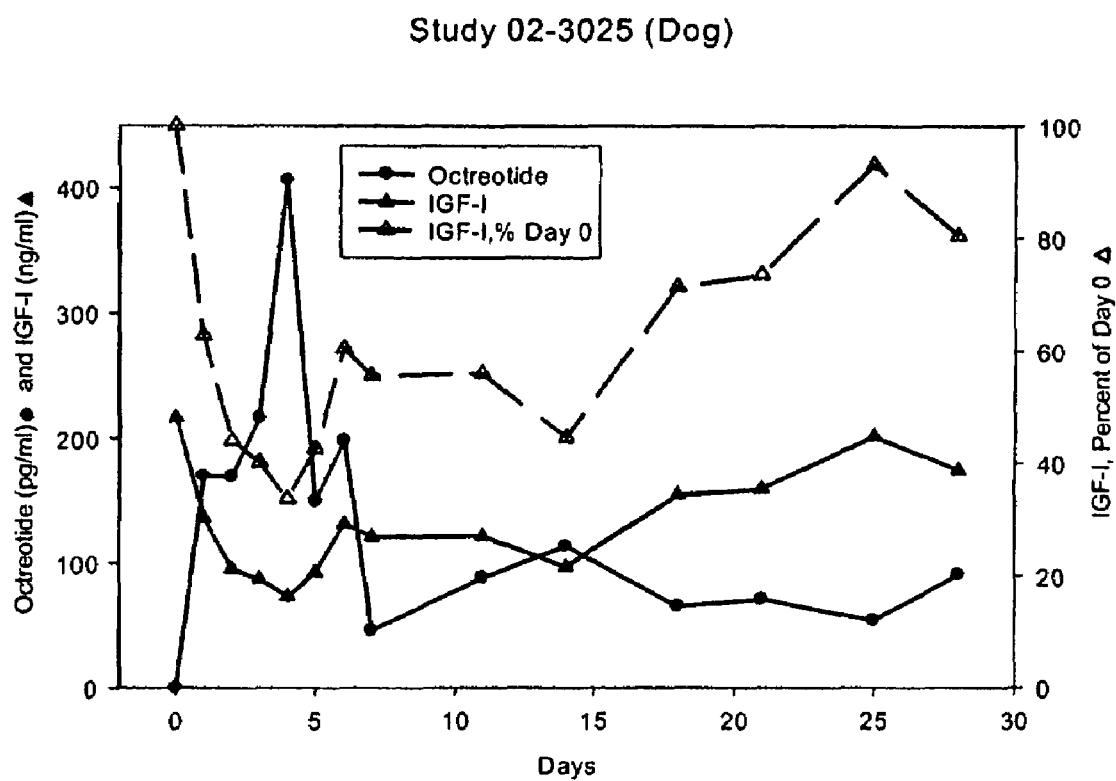
FIG. 6 is a graph showing octreotide and IGF-1 serum levels in a healthy dog implanted with an octreotide formulation of the present invention.

Serum analysis showed a peak of octreotide acetate at day 4 and detectable amounts of octreotide acetate at all intervals measured. IGF-1 concentrations decreased after implantation until day 4, then returned to pre-dose levels by day 25. IGF-1 levels declined from 40 to 90% of pre-implantation level, as can be seen in FIG. 6.

Example 6

Six-Month Implantation Study in Six Healthy Dogs

This example illustrates preparation of formulations of the present invention and their release of octreotide or pharmaceutically-acceptable salts thereof. Six healthy dogs were divided into two groups and implanted with one or two octreotide subdermal implants of the present invention, respectively. The octreotide subdermal implants had a water content of about 25.2% and contained about 60 mg octreotide acetate. The implants were removed six months after implantation. Blood samples (10 ml) to obtain the serum concentration of octreotide acetate, IGF-1 and GH were obtained once daily for the first 7 days following implantation followed by twice a week sampling for three weeks, and then once a week until conclusion of the six month period. Four days prior to implantation, baseline serum samples were taken as a control.

Figure 7:
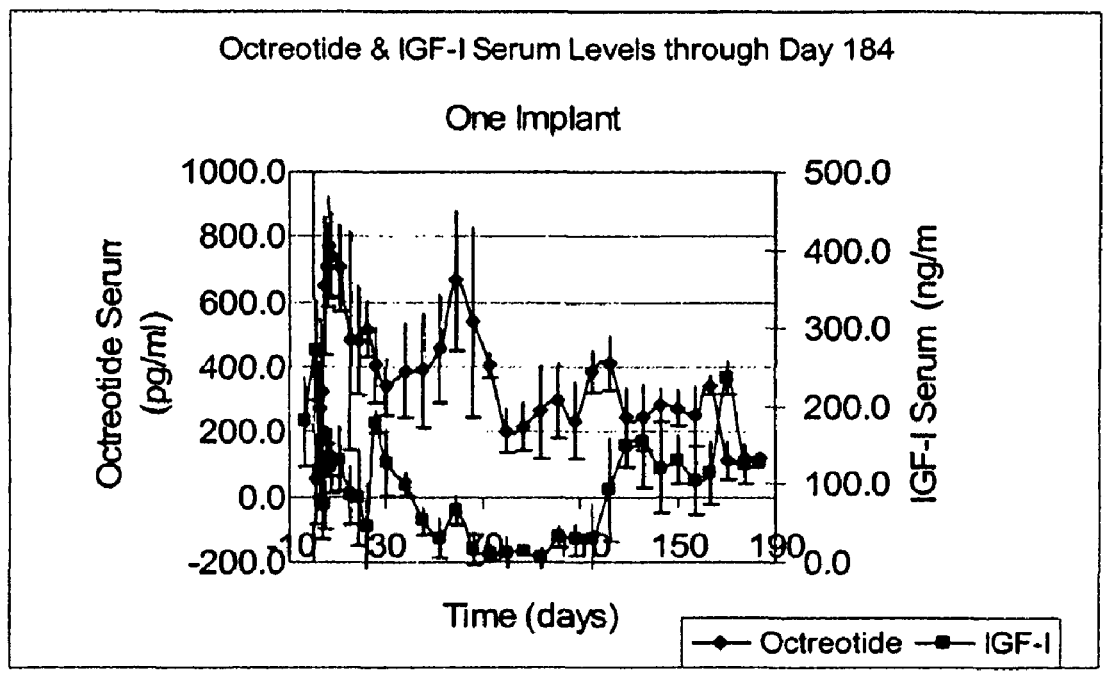
FIG. 7 is a graph showing octreotide and IGF-1 serum levels in a group of three healthy dogs implanted with one octreotide implant formulation of the present invention over a six month period.
Figure 8:
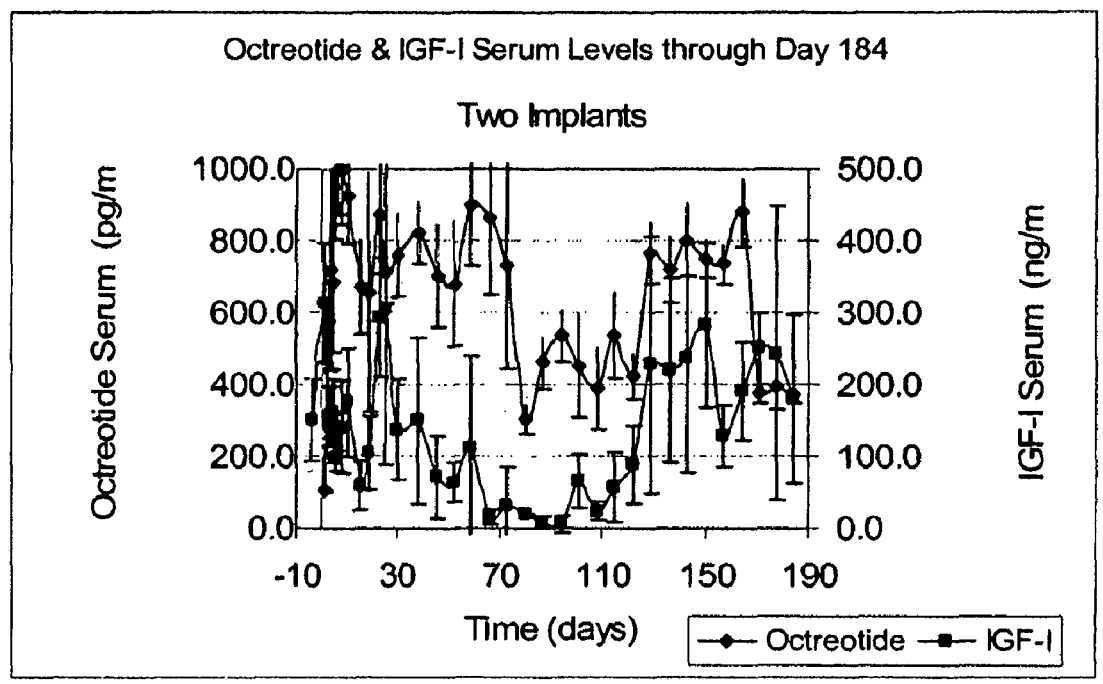
FIG. 8 is a graph showing octreotide and IGF-1 serum levels in a group of three healthy dogs implanted with two octreotide implant formulations of the present invention over a six month period.

Results indicate octreotide serum levels ranged from 200 to 700 μg/ml in dogs receiving one implant and 400 to 1000 μg/ml in dogs receiving two implants. IGF-1 levels were reduced as much as 90% in both treatment groups as can be seen in FIGS. 7 and 8. Measurement of serum GH levels was abandoned after about the first month of the study because levels in healthy animals are too low to detect further reductions. Clinical observations included the octreotide implant formulation was well-tolerated, food intake was normal, and no abnormal behavior was noted.

Example 7

Six-Month Implantation Study in Humans

This example illustrates preparation of formulations of the present invention and their release of octreotide or pharmaceutically acceptable salts thereof. A six-month study was conducted in eleven patients with acromegaly. One or two implants of the present invention were implanted subcutaneously in 11 patients diagnosed with acromegaly, who were previously treated with a commercially-available octreotide LAR formulation. Levels of GH and IGF-1 were measured at baseline and every month thereafter for a period of six months. Each implant contained approximately 60 mg of octreotide acetate in a copolymer of 20% HEMA and 79.5% HPMA, with an EWC of about 25.2%. The implants used in this study were about 44 mm in length in a dry state and 50 mm in length in a hydrated state. The diameters of the implants were about 2.8 mm in a dry state and about 3.5 to about 3.6 mm in a hydrated state. The implants were hydrated for a period of about 1 week prior to implantation.

The reference ranges for GH is up to 2.5 mg/L, age-independent. Table 4 illustrates the basal levels of GH in mg/L over six months after implantation of octreotide implants of the present invention. Patient No. 11 did not participate in the study due to failure to meet screening criteria.

TABLE 4

| Patient | Age | # Implants Rec'd | Screening GH (mg/L) | Visit 1 (Insertion) Basal GH (mg/L) | Visit 2 (Month 1) Basal GH (mg/L) | Visit 3 (Month 2) Basal GH (mg/L) | Visit 4 (Month 3) Basal GH (mg/L) | Visit 5 (Month 4) Basal GH (mg/L) | Visit 6 (Month 5) Basal GH (mg/L) | Visit 7 (Month 6) Basal GH (mg/L) |
|---|---|---|---|---|---|---|---|---|---|---|
| 001 | 39 | 1 | 26 | 16.3 | 0.9 | 1.5 | 1.1 | 1.1 | 1.1 | 2.1 |
| 002 | 38 | 2 | 17.8 | 20.7 | 1.4 | 0.2 | 0.3 | 0.2 | 0.3 | 0.48 |
| 003 | 49 | 1 | 67 | 55 | 2.8 | 3.1 | 3.3 | 5.0 | 5.3 | 5.8 |
| 004 | 47 | 2 | 7.9 | 7 | 2.6 | 3.8 | 2.8 | 3.7 | 4.0 | 2.4 |

TABLE 4-continued

| Patient | Age | # Implants Rec'd | Screening GH (mg/L) | Visit 1 (Insertion) Basal GH (mg/L) | Visit 2 (Month 1) Basal GH (mg/L) | Visit 3 (Month 2) Basal GH (mg/L) | Visit 4 (Month 3) Basal GH (mg/L) | Visit 5 (Month 4) Basal GH (mg/L) | Visit 6 (Month 5) Basal GH (mg/L) | Visit 7 (Month 6) Basal GH (mg/L) |
|---|---|---|---|---|---|---|---|---|---|---|
| 005 | 43 | 1 | 10.8 | 11 | 2.2 | 1.8 | 2.2 | 1.6 | 2.2 | 1.3 |
| 006 | 43 | 1 | 1.7 | 1.7 | 1.8 | 2.3 | 1.9 | 1.7 | 1.8 | 1.9 |
| 007 | 30 | 2 | 23.3 | 21.8 | 2.4 | 2.2 | 2.9 | 2.0 | 1.1 | 0.51 |
| 008 | 58 | 2 | 1.9 | 3.2 | 0.1 | 0.1 | 2.0 | 0.1 | 0.6 | 0.11 |
| 009 | 47 | 2 | 14.9 | 14.1 | 1.4 | 0.9 | 1.5 | 1.1 | 1.4 | 1.4 |
| 010 | 78 | 1 | 4 | 5.2 | 0.4 | 0.2 | 0.5 | 0.2 | 0.3 | 1.0 |
| 012 | 40 | 2 | 21.1 | 27.8 | 13.5 | 13.7 | 14 | 11.9 | 8.9 | 13.1 |
| mean | | | | 16.7 | 2.7 | 2.7 | 3.0 | 2.6 | 2.7 | 2.7 |

As shown above, by month six 89% of subjects exhibited normalized growth hormone levels. Reference ranges for IGF-1 are as follows: (i) 17-24 years old about 180-780 ng/mL; (ii) 25-39 years old about 114-400 ng/mL; (iii) 40-54 years old about 90-360 ng/mL; and (iv)>54 years old about 70-290 ng/mL.

Table 5 illustrates the basal levels of IGF-1 in ng/ml over six months after implantation of octreotide implants of the present invention.

IGF-1 levels were decreased in all patients, with normalization in 2 patients. The decrease was already observed at one month of therapy and the mean IGF-1 level was stable for the following 5 months. A comparison with decreases previously observed in the same patients while on the commercially available octreotide LAR formulation therapy was possible in 8 of the 9 patients. In 6 of the 8 patients, the percentage decrease in IGF-1 during the implant was greater than that while on the commercially-available octreotide LAR formu-

TABLE 5

| Patient | Age | # Implants Rec'd | Screening IGF-1 (ng/mL) | Visit 1 (Insertion) IGF-1 (ng/mL) | Visit 2 (Month 1) IGF-1 (ng/mL) | Visit 3 (Month 2) IGF-1 (ng/mL) | Visit 4 (Month 3) IGF-1 (ng/mL) | Visit 5 (Month 4) IGF-1 (ng/mL) | Visit 6 (Month 5) IGF-1 (ng/mL) | Visit 7 (Month 6) IGF-1 (ng/mL) |
|---|---|---|---|---|---|---|---|---|---|---|
| 001 | 39 | 1 | 1500 | 1500 | 820 | 600 | 900 | 880 | 790 | 750 |
| 002 | 38 | 2 | 1700 | 1300 | 210 | 180 | 190 | 170 | 130 | 230 |
| 003 | 49 | 1 | 1100 | 1200 | 610 | 550 | 750 | 660 | 850 | 660 |
| 004 | 47 | 2 | 1700 | 1800 | 1100 | 1200 | 1200 | 1100 | 910 | 990 |
| 005 | 43 | 1 | 1100 | 1000 | 450 | 510 | 480 | 600 | 490 | 430 |
| 006 | 43 | 1 | 520 | 580 | 470 | 430 | 440 | 480 | 440 | 460 |
| 007 | 30 | 2 | 1900 | 1700 | 440 | 560 | 560 | 600 | 430 | 520 |
| 008 | 58 | 2 | 1700 | 1200 | 220 | 240 | 170 | 260 | 160 | 240 |
| 009 | 47 | 2 | 2200 | 1800 | 590 | 830 | 950 | 930 | 1100 | 1100 |
| 010 | 78 | 1 | 590 | 490 | 270 | 260 | 230 | 310 | 220 | 350 |
| 012 | 40 | 2 | 1600 | 1600 | 1300 | 1500 | 1400 | 1700 | 1500 | 1400 |
| mean | | | | 1288 | 589 | 624 | 661 | 699 | 602 | 648 |

As shown above, by month six, 22% of subjects exhibited a normalized IGF-1 level.

Figure 9A:
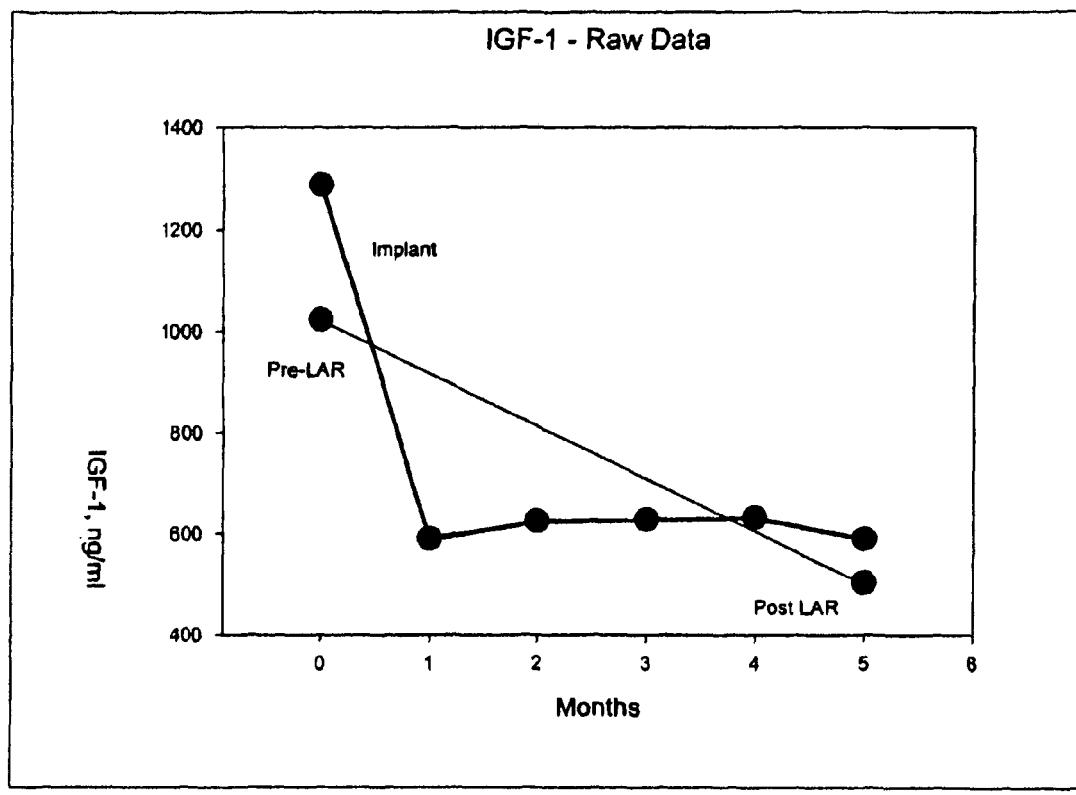
FIGS. 9A and 9B are graphs depicting the IGF-1 serum level and percent change in eleven human subjects with acromegaly over six months implanted with an octreotide formulation of the present invention, respectively.
Figure 9B:
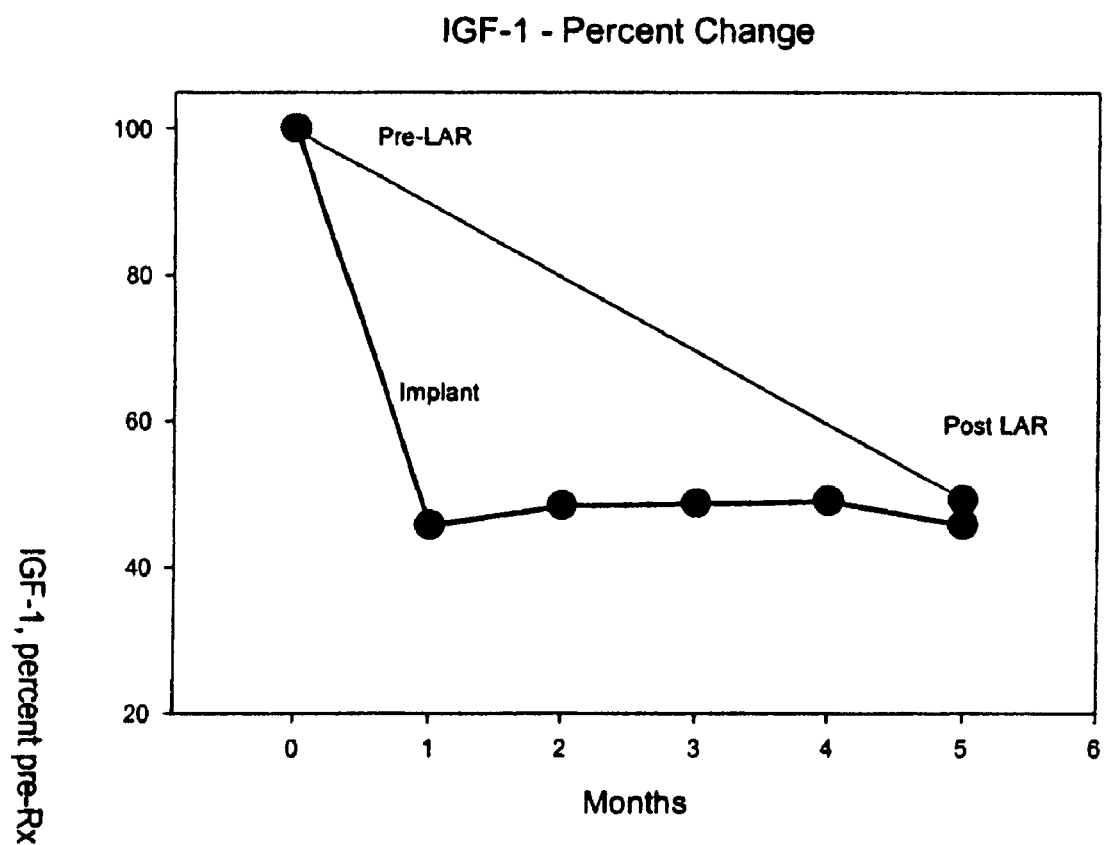

FIGS. 9A and 9B demonstrate a comparison of the octreotide implant of the present invention with a commercially-available formulation of octreotide acetate. The efficacy of the implant appeared to be at least as good as that of the commercially-available octreotide LAR formulation. The therapeutic effect of these implants continued successfully for the entire 6 months of the study duration.

lation, whereas in 2, it was less. After 6 months of therapy with the implant, GH levels in 3 patients were <1 ng/ml and in another 5, were <2.5 ng/ml. This compared favorably with the results on the commercially-available octreotide LAR formulation, where GH levels in only 2 patients were <1 ng/ml and in another 2, were under 2.5 ng/ml.

Levels of octreotide in the serum of patients was also measured, as shown in Table 6.

TABLE 6

| | | Month | | | | | | | |
|---|---|---|---|---|---|---|---|---|---|
| | | 1 | 2 | 3 | 4 | 5 | 6 | 7 | |
| #Implants | Patient ID | Visit 2 | Visit 3 | Visit 4 | Visit 5 | Visit 6 | Visit 7 | Visit 8 | Gender |
| 1 | Patient 1 | 1181 | 874.5 | 738.0 | 894.3 | 699.2 | 722.3 | 169.0 | F |
| 2 | Patient 2 | 2686 | 2478 | 1625 | 1833 | 1388 | 1203 | 280 | M |
| 1 | Patient 3 | 2570 | 2351 | 1332 | 980.5 | 1131 | 775.2 | 173 | F |
| 2 | Patient 4 | 4268 | 3308 | 2582 | 2650 | 2455 | 1984 | 166 | M |
| 1 | Patient 5 | 1218 | 1022 | 610.0 | 783.2 | 709.4 | 545.8 | 144 | F |
| 1 | Patient 6 | 1899 | 1445 | 1427 | 1123 | 1148 | 747.7 | 206 | F |
| 2 | Patient 7 | 5524 | 2621 | 3656 | 3141 | 2205 | 1466 | 154 | F |

TABLE 6-continued

| | | Month | | | | | | | |
|---|---|---|---|---|---|---|---|---|---|
| | | 1 | 2 | 3 | 4 | 5 | 6 | 7 | |
| #Implants | Patient ID | Visit 2 | Visit 3 | Visit 4 | Visit 5 | Visit 6 | Visit 7 | Visit 8 | Gender |
| 2 | Patient 8 | 8684 | 3387 | 4899 | 3336 | 3454 | 1765 | 170 | F |
| 2 | Patient 9 | 3850 | 860.6 | 2638 | 1766 | 1729 | 1510 | 203 | M |
| 1 | Patient 10 | 2055 | 1628 | 1192 | 863.9 | 1641 | 1231 | 1130 | F |
| 2 | Patient 12 | 2527 | 1366 | 2006 | 962.8 | 1484 | 1156 | 189 | M |

Figure 10:
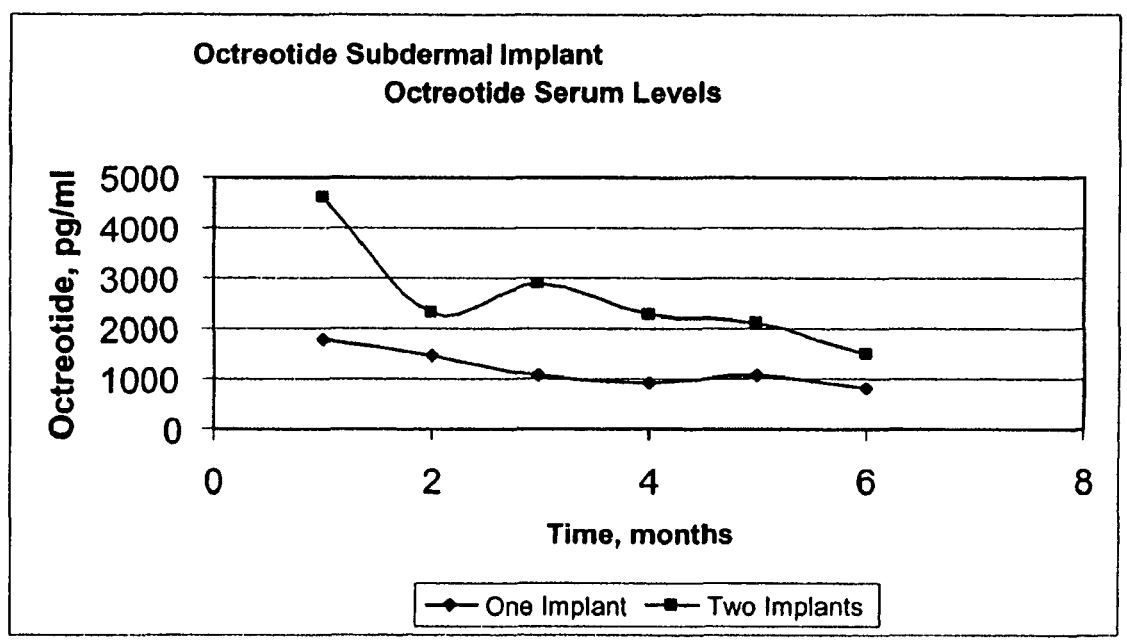
FIG. 10 is a graph depicting octreotide serum levels in eleven human subjects with acromegaly over six months implanted with an octreotide formulation of the present invention.

A comparison of the octreotide levels achieved with one and two implants is depicted in the graph in FIG. 10. Overall, results indicated that the octreotide implant of the present invention is at least as effective as the commercially available LAR formulation of octreotide acetate in reducing GH levels and IGF-1 levels in patients with acromegaly.

Example 8

In Vitro Octreotide Delivery Using Dry Implants

This example illustrates preparation of formulations of the present invention and their release of octreotide or pharmaceutically acceptable salts thereof. Two healthy dogs were implanted with one octreotide subdermal implant of the present invention. The implants were not hydrated prior to implantation. The octreotide subdermal implants were composed of about 59.5% HPMA and about 40% HEMA and had an equilibrium water content of about 27.6%. The implants contained about 84 mg of octreotide acetate, hydroxypropylcellulose and magnesium stearate. The implants were removed six months after implantation. Blood samples (10 ml) were drawn to obtain the serum concentration of octreotide acetate and IGF-1 once daily every other day for the first four weeks following implantation followed by twice a week sampling for four weeks, and then once a week until conclusion of the six month period. Two days prior to implantation, baseline serum samples were taken as a control.

Figure 11:
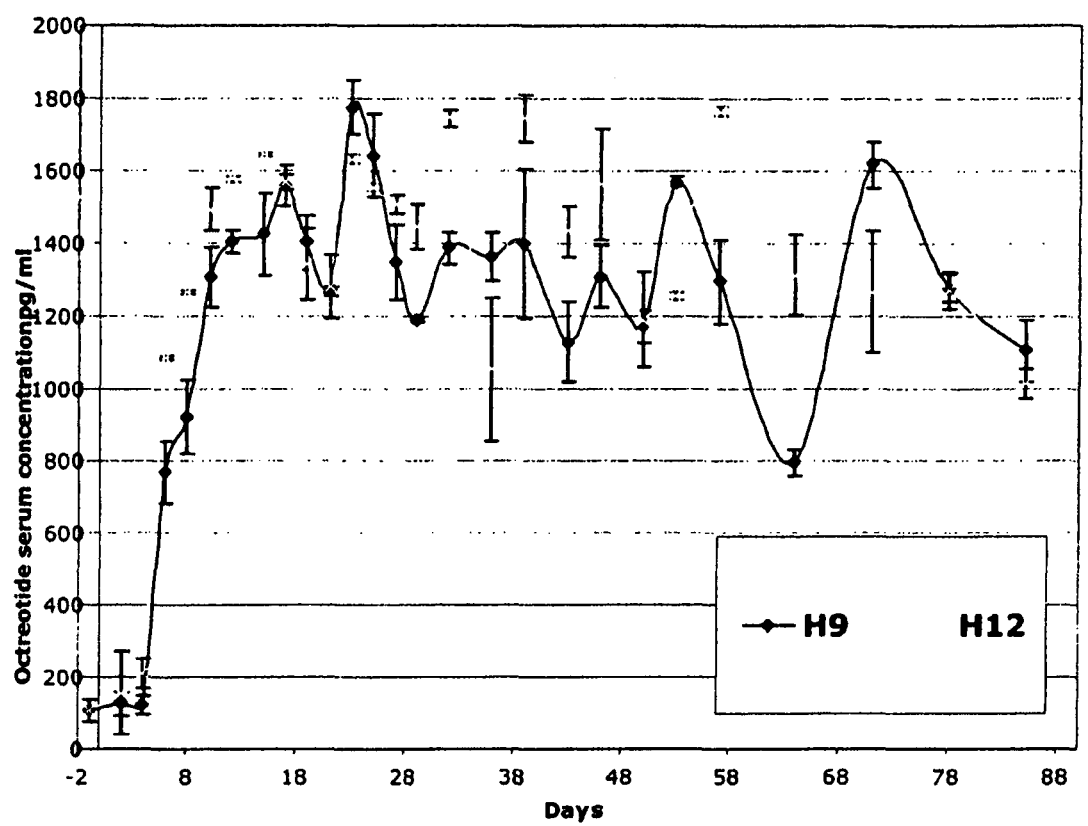
FIG. 11 is a graph depicting octreotide serum levels in two dogs over six months implanted with an octreotide formulation of the present invention.
Figure 12:
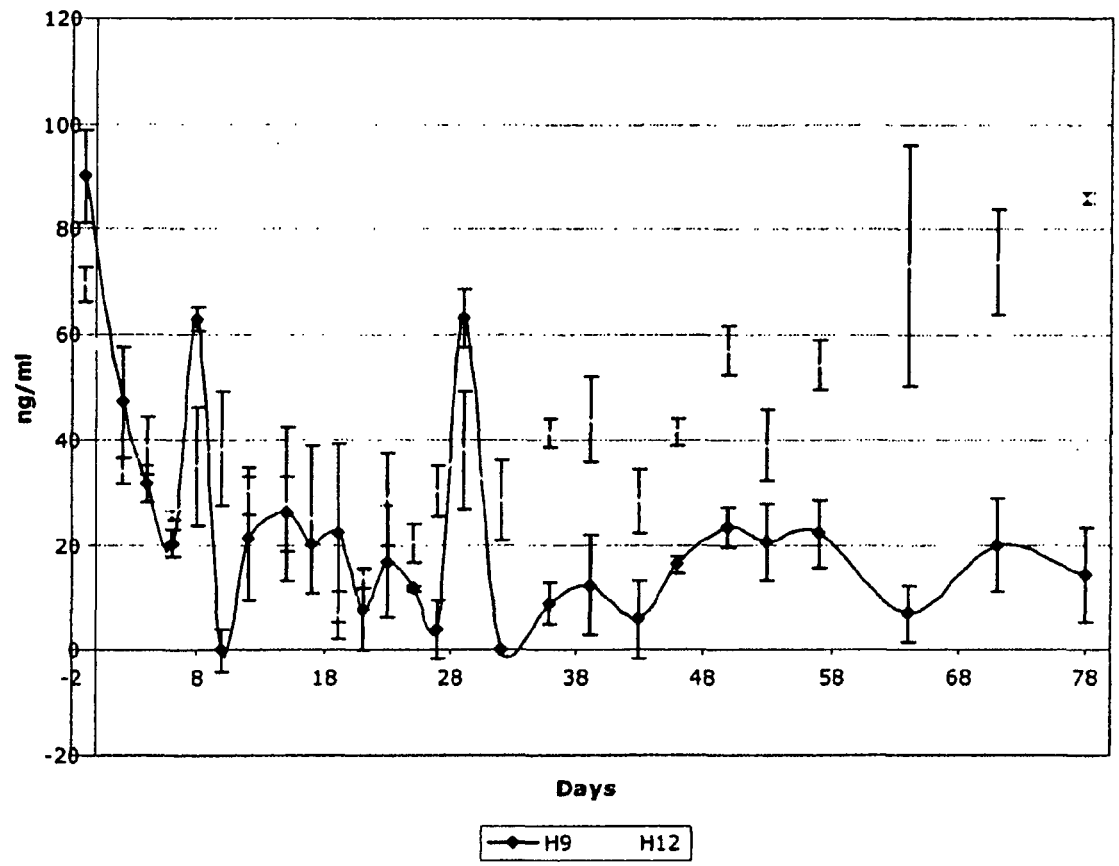
FIG. 12 is a graph depicting IGF-1 serum levels in two dogs over six months implanted with an octreotide formulation of the present invention.

FIG. 11 shows the octreotide levels in the serum of the dogs and FIG. 12 shows the levels of IGF-1 in the dogs.

Example 9

Implant Compositions

Possible compositions for the implants of the invention include, for example, those listed in Table 7, below. Implant cartridges greater than about 3.2-3.4 mm (dry) are aided by the use of release agents, e.g., vitamin E TPGS, during the formation process.

TABLE 7

| | Composition of Implant | |
|---|---|---|
| | Small Implant | Large Implant |
| API | 60 mg Octreotide Acetate | 84 mg Octreotide Acetate |
| Pellet Excipients | 10% Hydroxypropyl cellulose (~6.8 mg/implant) 2% Magnesium Stearate (~1.3 mg/implant) | 10% Hydroxypropyl cellulose (~9.5 mg/implant) 2% Magnesium Stearate (~2 mg/implant) |
| Monomer Mixture Composition | 20% HEMA 79.5% HPMA 0.5% TMPTMA | 40% HEMA 59.5% HPMA 0.5% TMPTMA |

TABLE 7-continued

| | Composition of Implant | |
|---|---|---|
| | Small Implant | Large Implant |
| | Added to mixture: 1% Triton X-100 0.3% BME 0.1% P-16 | Added to mixture: 1% Vitamin E TPGS 0.3% BME 0.1% P-16 |
| Dry Implant Size | 2.8 mm × 43 mm | 3.4 mm × 43 mm |
| Surface Area | 378 mm$^2$ | 459 mm$^2$ |
| Hydrated Implant Size | 3.4 mm × 50 mm | 4.3 mm × 50 mm |
| Surface Area | 534 mm$^2$ | 675 mm$^2$ |
| EWC | 26.0% | 28.7% |
| Sterilization | Gamma Irradiation | Gamma Irradiation |
| Packaging Solution | Implants packaged dry in 2 compartment package with 0.9% saline solution in the second compartment. Implant is combined with saline 7-14 days prior to implantation to allow for implant hydration. | Implants packaged dry in 2 compartment package with 0.9% saline solution in the second compartment. Implant is combined with saline 3-7 days prior to implantation to allow for implant hydration. |
| Packaging | Divided Pouch with LF4835W Foil Barrier/FR5500 PET/PE Clear Sleeve as components. LF4835W - DMF # 15796 FR5500 - Approved for food contact | Divided Pouch with JT48FLLP Foil Barrier/IT-CB259B Aluminum Oxide CTD PET Clear Sleeve as components. For use in sterile medical packaging |
| Average Daily Release Rate | 130 µg/day for 6 months | 250 µg/day for 6 months |

Example 10

An Open-Label Study to the Evaluate the Pharmacokinetic and Pharmacodynamic Response of a Hydrated and Non-Hydrated 84 mg Octreotide Implant in Patients with Acromegaly Approximately 30 patients with acromegaly were enrolled after written informed consent was obtained. Patients were divided in 2 groups per the study randomization schedule: 15 patients received one hydrated 84 mg octreotide implant and 15 patients received one non-hydrated 84 mg octreotide implant. Eligible patients received the implant within 7 days of their screening visit. The octreotide implant was inserted subcutaneously in the inner aspect of their non-dominant arm under local anesthesia. Blood samples for the determination of IGF-1, GH and octreotide serum concentrations were collected at predetermined time points within the first 6 weeks after implantation. Patients then return for visits at Week 8, 12, 16, 20 and 24 to have blood samples collected for the determination of IGF-1, GH and octreotide serum concentrations, as well as safety assessments. At the end of the 6-month (24-week) treatment phase, the implant will be removed. Following implant removal, the patient will be instructed to return in 4 weeks for the End of Study Visit (Week 28). Safety and efficacy will be carefully monitored throughout the study.

Investigational Products:
Hydrated octreotide implant (84 mg octreotide acetate) for subcutaneous implantation
Non-hydrated octreotide implant (84 mg octreotide acetate) for subcutaneous implantation Duration of Treatment:
Eligible patients receive one implant, either hydrated or non-hydrated. At the end of the 6-month (24-week) treatment phase, the implant will be removed. Following implant removal, the patient will be instructed to return in 4 weeks for the End of Study Visit.

Criteria for Inclusion:
1. Male and female patients with acromegaly
2. Must be ≧18 years of age
3. Confirmed diagnosis of a growth hormone-secreting tumor (elevation of IGF-1 level ≧20% above upper limit of age- and sex-adjusted normal value and either a post-glucose GH of ≧1.0 ng/ml or a pituitary tumor demonstrable on MRI). If patient has undergone pituitary surgery and has residual tumor present, it must be at least 3 mm in distance from the optic chiasm (unless patient is not a surgical candidate) and IGF-1 level must be elevated as described above. If no residual tumor is present or patient is inoperable then patient must meet both IGF-1 and GH criteria as described above.
4. Must be either a full or partial responder to octreotide demonstrated by historical laboratory values, as defined below:
   a. Full responder: suppression of serum IGF-1 to normal age- and sex-adjusted levels and suppression of serum GH to <1.0 ng/ml after OGTT
   b. Partial responder: a ≧30% decrease in IGF-1 and GH values when compared to pre-treatment values, but not meeting criteria for full responder
   c. OR
   d. Must be a responder to octreotide demonstrated by laboratory values obtained via an acute aqueous test during the Screening Visit for octreotide naïve patients or patients in whom response to octreotide is unknown, as defined below:
   e. Responder via acute aqueous test: a ≧30% decrease in GH values at any time point of the 4 hour test period in response to a subcutaneous injection of 100 μg of aqueous octreotide
5. Must be able to communicate, provide written informed consent, and willing to participate and comply with study requirements
6. Patient is eligible to participate in the opinion of the Investigator Criteria for Exclusion:
1. Women who are pregnant, lactating, or of child-bearing potential who are not practicing a medically acceptable method of birth control
2. Patients with pituitary surgery less than 12 weeks prior to screening
3. Patients with liver disease (e.g., cirrhosis, chronic active or persistent hepatitis or persistent abnormalities of ALT, AST (level >2× normal), alkaline phosphatase (level >2× normal), or direct bilirubin (level >1.5× normal)
4. Other laboratory values considered by the Investigator or Sponsor to be clinically significant
5. Patients with unstable angina, sustained ventricular arrhythmias, heart failure (NYHA III and IV), or a history of an acute myocardial infarction within 3 months of screening
6. Patients with symptomatic cholelithiasis
7. Patients with a history of drug or alcohol abuse within 6 months of screening
8. Patients who have received any investigational drug within 1 month of screening
9. Patients receiving radiotherapy for their pituitary tumor at any time before screening
10. Patients who have discontinued octreotide due to tolerability or efficacy issues.

Figure 13:
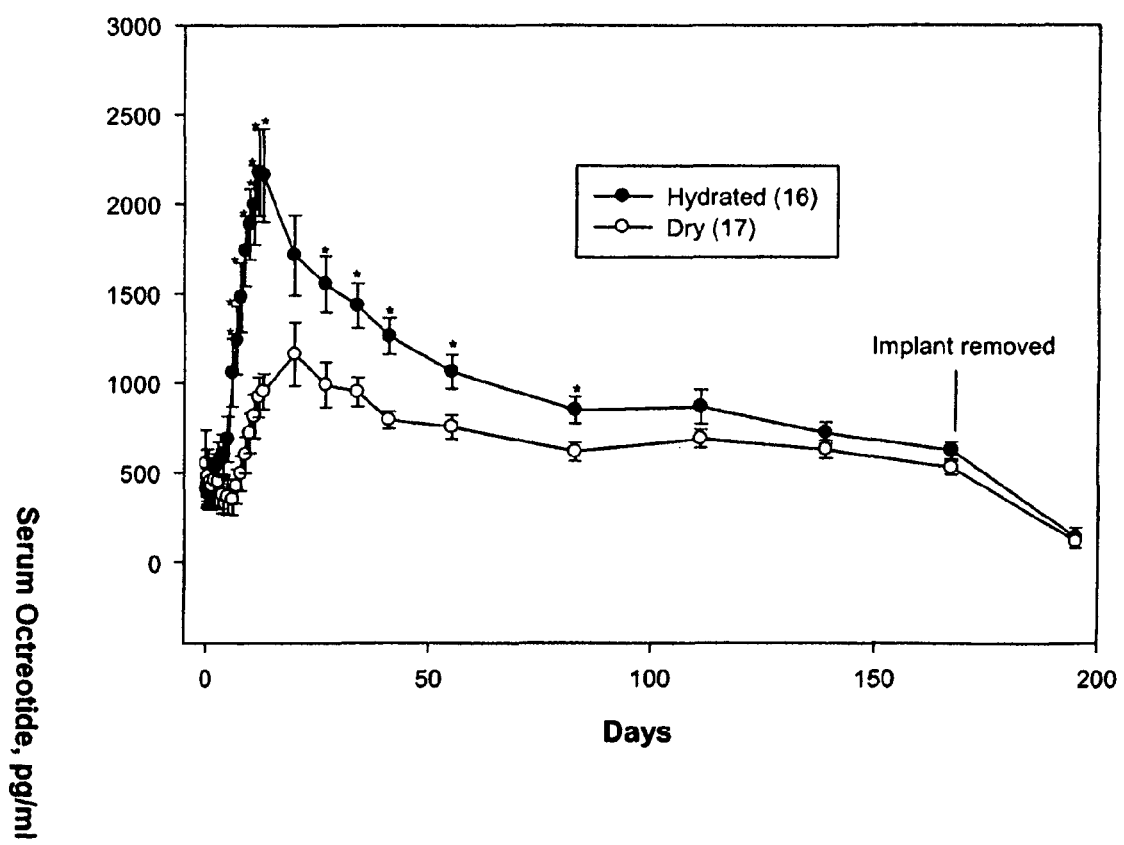
FIG. 13 is a graph showing serum octreotide levels after hydrated implant delivery and dry implant delivery (see also Table 6).
Figure 14:
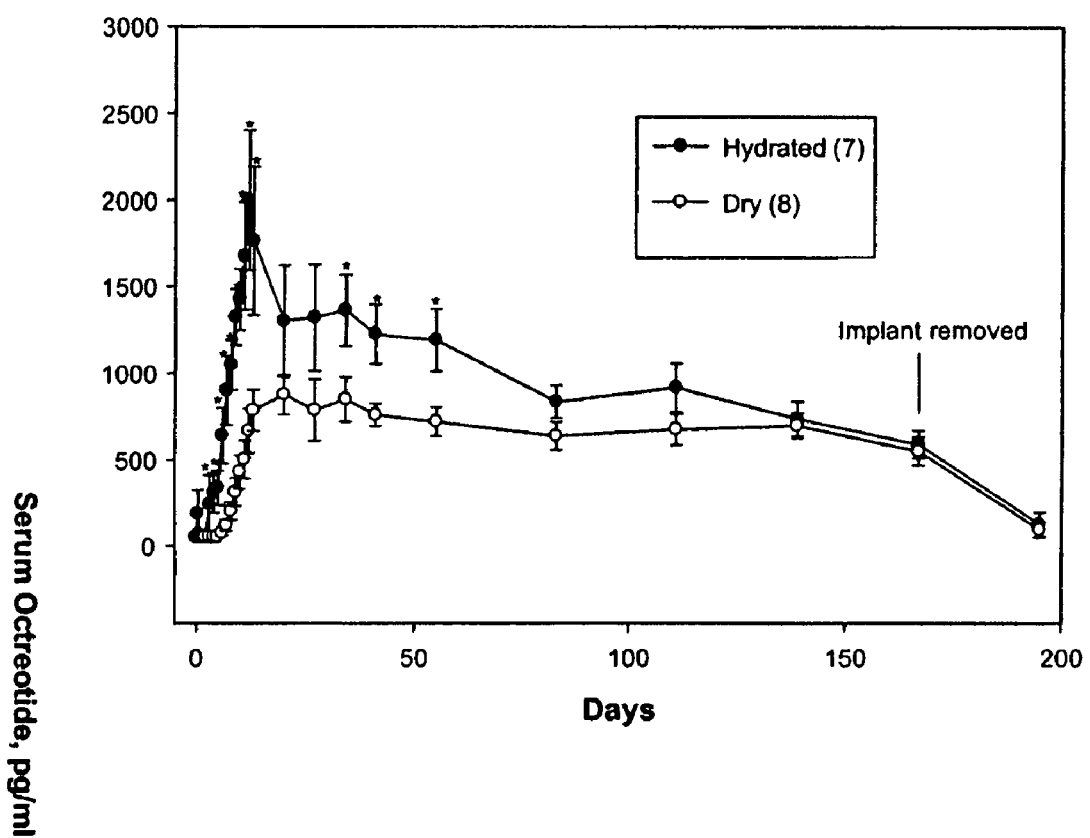
FIG. 14 is a graph showing serum octreotide levels after hydrated implant delivery and dry implant delivery (see also Table 6).

Serum levels of octreotide were determined (see FIGS. 13 and 14 for graphical data).

Figure 15A:
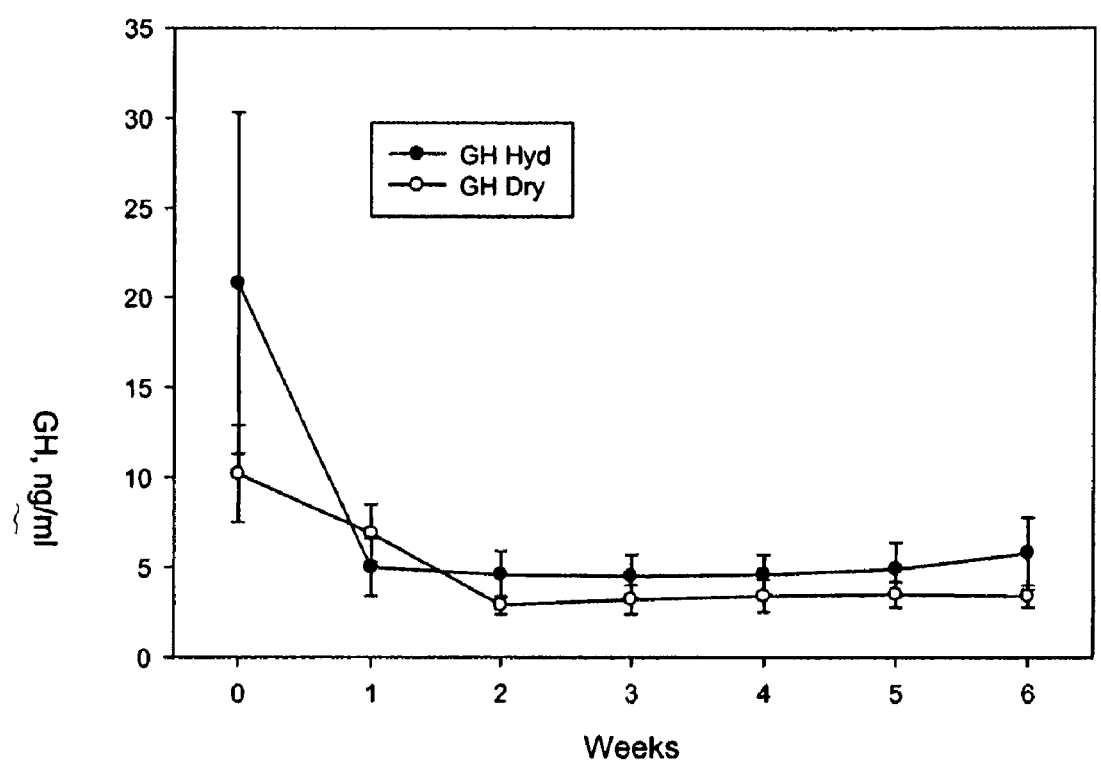
FIG. 15 are graphs showing the level of growth hormone after delivery of octreotide by hydrated and dry implants (GH concentration, upper panel; % GH decrease, bottom panel).
Figure 15B:
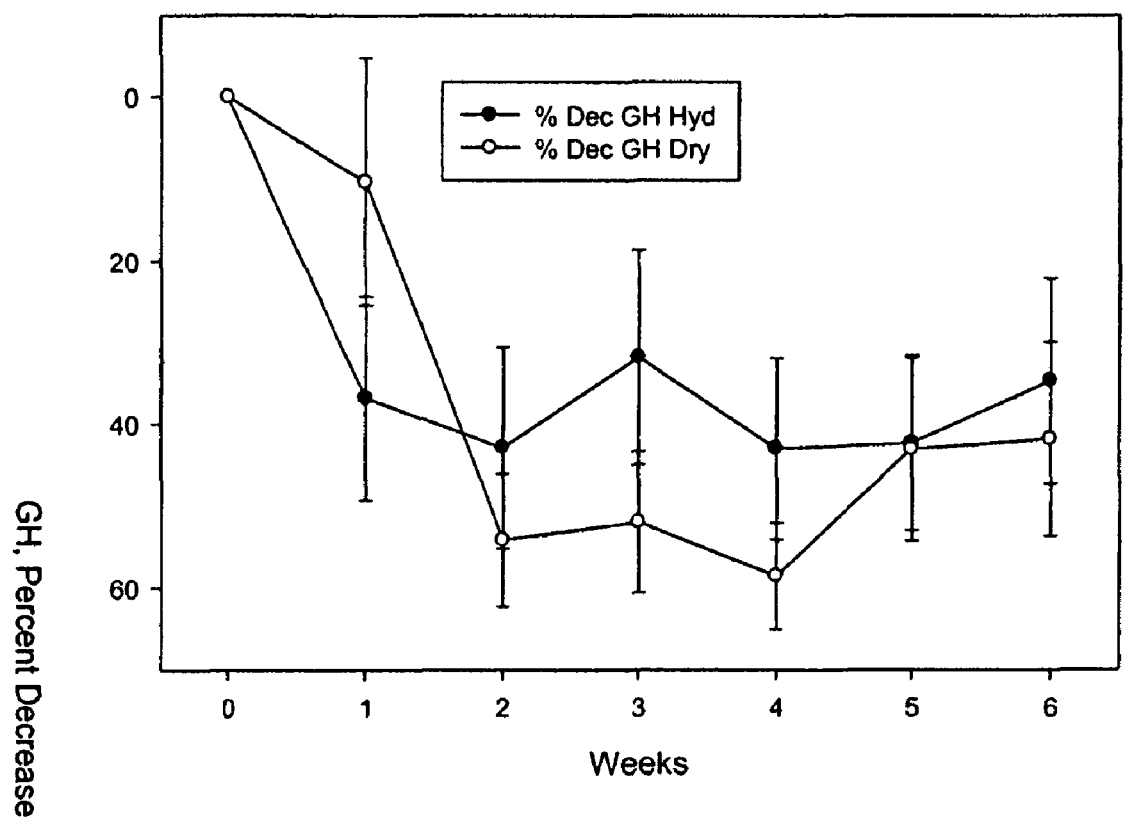
Figure 16A:
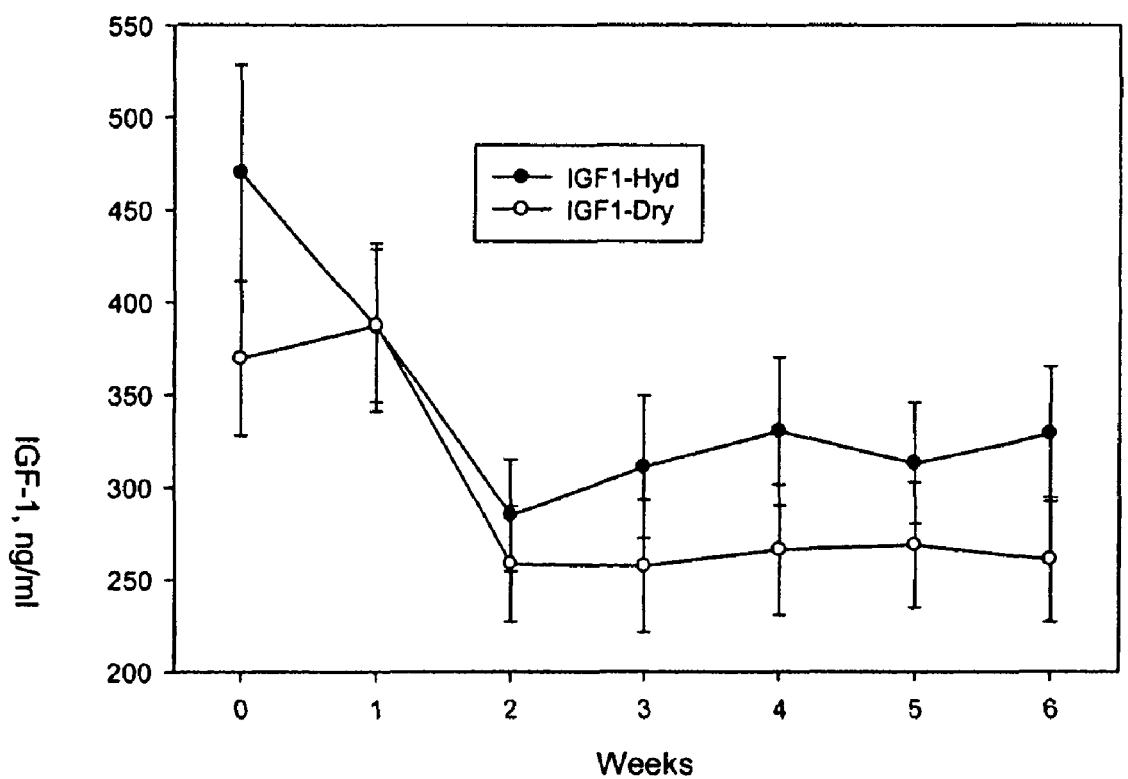
FIG. 16 are graphs showing the level of insulin-like growth factor 1 (IGF-1) after delivery of octreotide by hydrated and dry implants (IGF-1 concentration, upper panel; standard deviation, bottom panel).
Figure 16B:
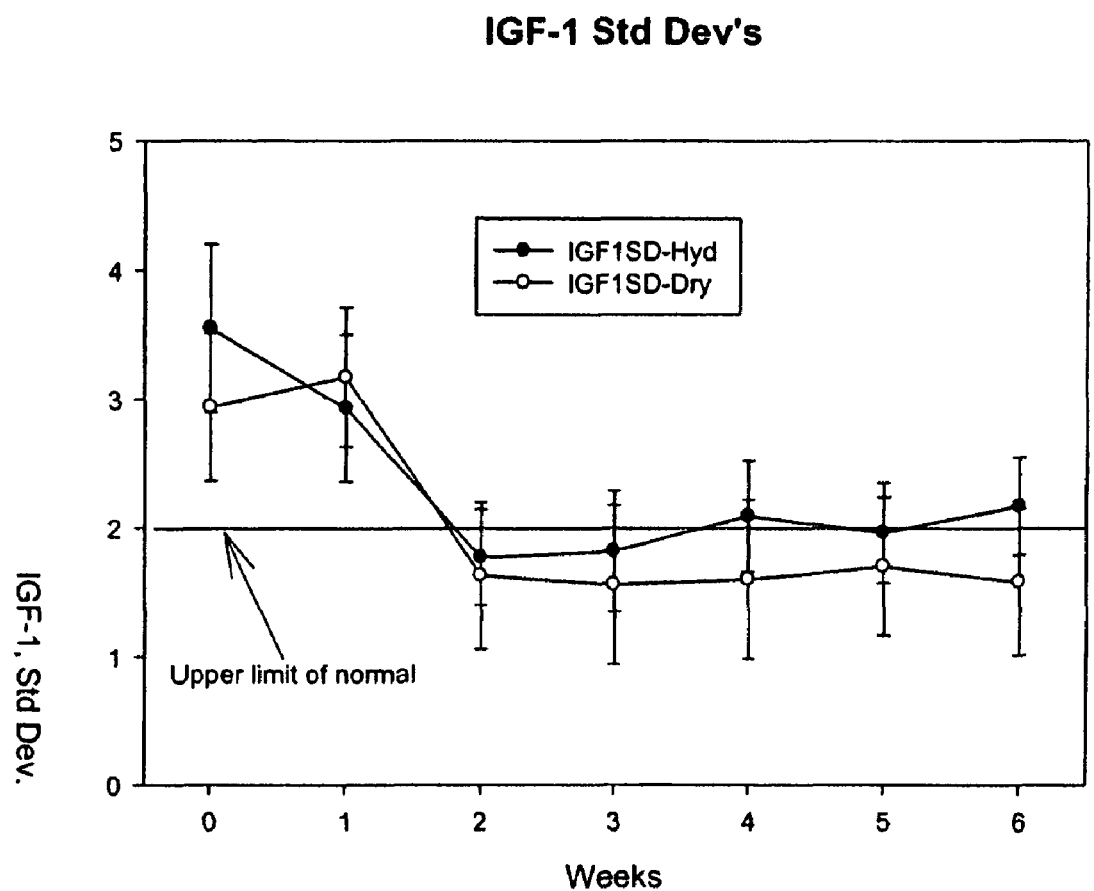
Figure 17A:
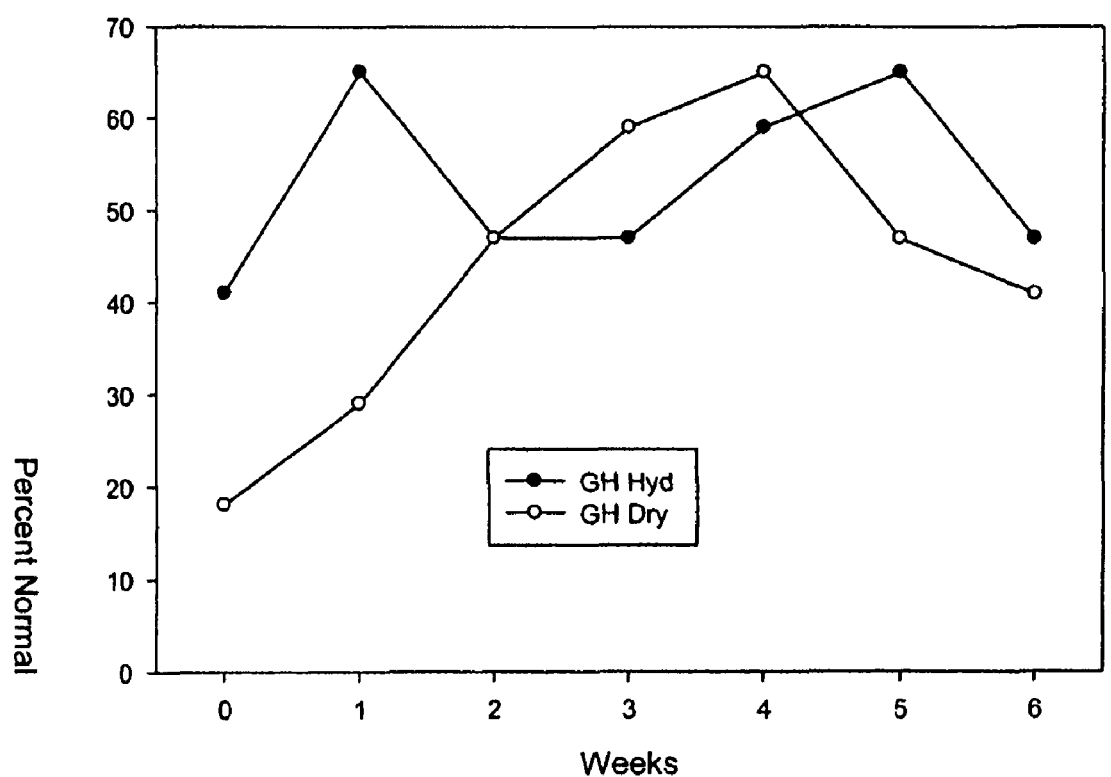
FIG. 17 are graphs showing the level of insulin-like growth factor 1 (IGF-1) after delivery of octreotide by hydrated and dry implants (both panels show data from studies with values expressed as the percent of normal IGF-1 levels).
Figure 17B:
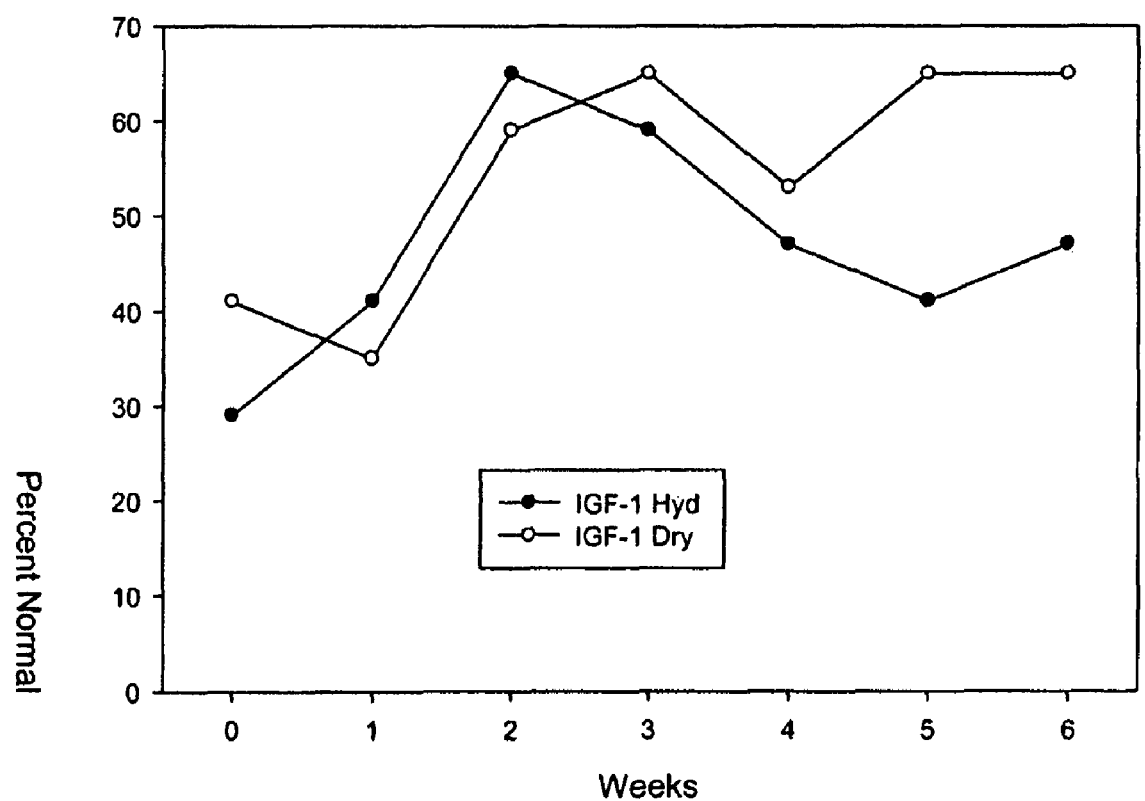

The efficacy of cytokine concentration modulation after the octreotide implant was inserted, either in the dry form or after hydration, is shown in FIGS. 15, 16, and 17.

Example 11

Treatment of Tumors with Octreotide

Sandostatin LAR® Depot, as indicated on the FDA label (the entire contents of which are herein incorporated by reference), is a long-acting dosage form consisting of microspheres of the biodegradable glucose star polymer, D,L-lactic and glycolic acids copolymer, containing octreotide. It maintains all of the clinical and pharmacological characteristics of the immediate-release dosage form Sandostatin® (octreotide acetate) Injection with the added feature of slow release of octreotide from the site of injection, reducing the need for frequent administration. This slow release occurs as the polymer biodegrades, primarily through hydrolysis. Sandostatin LAR® Depot is designed to be injected intramuscularly (intragluteally) once every four weeks.

Octreotide exerts pharmacologic actions similar to the natural hormone, somatostatin. It is an even more potent inhibitor of growth hormone, glucagon, and insulin than somatostatin. Like somatostatin, it also suppresses LH response to GnRH, decreases splanchnic blood flow, and inhibits release of serotonin, gastrin, vasoactive intestinal peptide, secretin, motilin, and pancreatic polypeptide. By virtue of these pharmacological actions, octreotide has been used to treat the symptoms associated with, for example, metastatic carcinoid tumors (flushing and diarrhea), and Vasoactive Intestinal Peptide (VIP) secreting adenomas (watery diarrhea). Octreotide substantially reduces and in many cases can normalize growth hormone and/or IGF-I (somatomedin C) levels in patients with acromegaly. Single doses of Sandostatin® Injection given subcutaneously have been shown to inhibit gallbladder contractility and to decrease bile secretion in normal volunteers.

In patients with acromegaly, the pharmacokinetics differ somewhat from those in healthy volunteers. A mean peak concentration of 2.8 ng/mL (100 mcg dose) was reached in 0.7 hours after subcutaneous dosing. The volume of distribution (Vdss) was estimated to be 21.6±8.5 L and the total body clearance was increased to 18 L/h. The mean percent of the drug bound was 41.2%. The disposition and elimination half-lives were similar to normals.

Treating these tumors typically involves surgery as the first-line therapy. Failing surgery, patients are usually given octreotide injections (such as S-Lar). Chemotherapy may also prove beneficial- and does so in about 30% of patients.

Patients with carcinoid tumors were treated with six doses of S-Lar at 10, 20, or 30 mg given by i.m. injection every 4 weeks. Resulting serum concentrations were 1.2, 2.5, and 4.2 ng/mL. Steady state was achieved after two doses at 20 or 30 mg and after 3 doses at 10 mg.

Treatment with S-Lar reduced daily stool frequency to 2-2.5 stools/day, decreased mean daily flushing episodes to 0.5 to 1 episode/day, and reduced median 24-hr urinary 5-HIAA levels by 38-50%. It should be noted that over a 6 m trial, 50-70% of patients who completed the trial required supplemental Sandostatin injections to help control exacerbation of symptoms.

Although the present invention has been described in considerable detail with reference to certain preferred embodiments thereof, other versions are possible. Therefore the spirit and scope of the appended claims should not be limited to the description and the preferred versions contained within this specification.

What is claimed is:

1. A method of delivering octreotide to a subject with a substantially zero-order release profile over an extended period of time, but no less than about six months, the method comprising subcutaneously implanting in the subject at least one implantable device, wherein the at least one implantable device comprises a composition comprising octreotide and hydroxypropylcellulose, wherein the composition is encased in a hydrophilic polymer comprising a co-polymer obtained from the co-polymerization of a mixture comprising at least two hydrophilic, ethylenically unsaturated monomers, and wherein the implantable device is implanted in a dry state, such that the subject receives on a daily basis over a period of at least about six months dose amounts of octreotide, which are effective to treat the subject.

2. The method of claim 1, wherein at least one of the two hydrophilic, ethylenically unsaturated monomers is a methacrylate-based monomer.

3. The method of claim 1, wherein the octreotide is in free form, salt form or in the form of a complex thereof.

4. The method of claim 1, wherein the octreotide is octreotide acetate.

5. The method of claim 1, wherein the subject is afflicted with a GH or IGF-1 hormone disorder or its symptoms.

6. The method of claim 5, wherein the GH or IGF-1 disorder is acromegaly.

7. The method of claim 1, wherein the subject receives octreotide at an average rate ranging from about 75 μg per day to about 300 μg per day over a period of at least about six months.

8. The method of claim 1, wherein the dose amounts of octreotide received by the subject result in octreotide serum levels ranging from about 0.5 ng/ml to about 2 ng/ml.

9. The method of claim 1, wherein the subject receives an effective amount of octreotide for a period of at least about twelve months.

10. The method of claim 1, wherein the dose amounts of octreotide received by the subject result in octreotide serum levels ranging from about 0.8 ng/ml to about 1.8 ng/ml.

11. The method of claim 1, wherein the dose amounts of octreotide received by the subject result in $C_{max}$ for octreotide serum levels below about 1.3 ng/ml.

12. The method of claim 1, wherein the dose amounts of octreotide received by the subject result in $C_{max}$ for octreotide serum levels below about 1.0 ng/ml.

13. The method of claim 1, wherein release of octreotide occurs at least three to about ten days after implantation.

14. The method of claim 1, wherein the subject is afflicted with a condition selected from the group consisting of: carcinoid syndrome, VIPomas, neuroendocrine tumors, proliferative diabetic retinopathy, rosacea, pancreatitis, gastrointestinal bleeding, pancreatic and intestinal fistulas, Graves-Basedow opthalmopathy, glaucoma, and symptoms associated with chemotherapy or AIDS.

15. The method of claim 1, wherein said hydrophilic, ethylenically unsaturated monomers are selected from 2-hydroxyethyl methacrylate and hydroxypropyl methacrylate monomers.

16. The method of claim 1, wherein said copolymer comprises about 20% of 2-hydroxyethyl methacrylate and about 80% hydroxypropyl methacrylate.

17. A method of delivering octreotide to a subject with a substantially zero-order release profile over an extended period of time, but no less than about six months, the method comprising subcutaneously implanting in the subject at least one implantable device, wherein the at least one implantable device comprises a composition comprising hydroxypropylcellulose and from about 20 to about 150 mg of octreotide, in free form or salt form, wherein the composition is encased in a hydrophilic polymer comprising a co-polymer obtained from the co-polymerization of a mixture comprising at least two hydrophilic, ethylenically unsaturated monomers, and wherein the implantable device is implanted in a dry state, such that the subject receives on a daily basis over a period of at least about six months dose amounts of octreotide, which are effective to treat the subject.

* * * * *